(12) United States Patent
Liu et al.

(10) Patent No.: US 12,175,679 B2
(45) Date of Patent: Dec. 24, 2024

(54) 3D SEGMENTATION OF LESIONS IN CT IMAGES USING SELF-SUPERVISED PRETRAINING WITH AUGMENTATION

(71) Applicant: Merck Sharp & Dohme LLC, Rahway, NJ (US)

(72) Inventors: Yiqiao Liu, Pittsburgh, PA (US); Antong Chen, Blue Bell, PA (US); Gregory Goldmacher, Lincoln, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 18/522,131

(22) Filed: Nov. 28, 2023

(65) Prior Publication Data

US 2024/0177320 A1    May 30, 2024

Related U.S. Application Data

(60) Provisional application No. 63/385,391, filed on Nov. 29, 2022.

(51) Int. Cl.
*G06T 7/12* (2017.01)
*G06T 7/00* (2017.01)
(Continued)

(52) U.S. Cl.
CPC .............. *G06T 7/12* (2017.01); *G06T 7/0012* (2013.01); *G06T 7/13* (2017.01); *G06T 7/60* (2013.01);
(Continued)

(58) Field of Classification Search
CPC . G06T 2207/30096; G06T 2207/20081; G06T 2207/20084; G06T 7/11;
(Continued)

(56) References Cited

U.S. PATENT DOCUMENTS

2021/0326653 A1\* 10/2021 Zhou .................... G06F 18/2155
2022/0319008 A1\* 10/2022 Bengtsson ........... A61B 5/4848

FOREIGN PATENT DOCUMENTS

KR    10-2021-0141650 A    11/2021
KR    10-2022-0144687 A    10/2022

OTHER PUBLICATIONS

Chaitanya, Krishna, et al. "Contrastive learning of global and local features for medical image segmentation with limited annotations ." Advances in neural information processing systems 33 (2020): 12546-12558. (Year: 2020).\*

(Continued)

*Primary Examiner* — Aaron W Carter
*Assistant Examiner* — Courtney Joan Nelson
(74) *Attorney, Agent, or Firm* — Fenwick & West LLP

(57) ABSTRACT

A method or system for training a convolutional neural network (CNN) for medical imaging analysis. The system pre-trains the CNN's encoder using a dataset of unlabeled 3D medical images. Each 3D image includes an annotated slice delineating a boundary of a lesion and multiple non-annotated 2D slices above and below the annotated slice. The system then fine-tunes the pre-trained encoder using an annotated 2D image dataset. The annotated 2D image dataset includes multiple 2D slices of lesions, each including an annotation that delineates a boundary of a corresponding lesion.

17 Claims, 13 Drawing Sheets

(51) Int. Cl.
*G06T 7/13* (2017.01)
*G06T 7/60* (2017.01)
*G16H 30/40* (2018.01)

(52) U.S. Cl.
CPC ... *G16H 30/40* (2018.01); *G06T 2207/20084* (2013.01); *G06T 2207/30096* (2013.01)

(58) Field of Classification Search
CPC ... G06T 7/12; G06T 7/13; G06T 2207/20076; G06T 7/174; G06T 7/0012; G06T 7/60; G06F 18/241; G06N 3/08; G06N 20/00; G16H 30/40; G16H 50/20
See application file for complete search history.

(56) References Cited

OTHER PUBLICATIONS

Zeng, Dewen, et al. "Positional contrastive learning for volumetric medical image segmentation." Medical Image Computing and Computer Assisted Intervention-MICCAI 2021: 24th International Conference, Strasbourg, France, Sep. 27-Oct. 1, 2021, Proceedings, Part II 24. Springer International (Year: 2021) International Publishing, 2021. (Year: 2021).*
PCT International Search Report and Written Opinion, PCT Application No. PCT/US2023/081447, Apr. 4, 2024, 12 pages.
Schlegl, T. et al. "Unsupervised pre-training across image domains improves lung tissue classification," *International MICCAI Workshop on Medical Computer Vision*, Sep. 18, 2014, 12 pages.
Zeng, D. et al. "Positional contrastive learning for volumetric medical image segmentation," *Medical Image Computing and Computer Assisted Intervention*, Sep. 28, 2021, 12 pages.

* cited by examiner

3D SEGMENTATION OF LESIONS IN CT IMAGES USING SELF-SUPERVISED PRETRAINING WITH AUGMENTATION

CROSS REFERENCE OF RELATED APPLICATION

This application claims priority to U.S. Provisional Patent Application 63/385,391, filed Nov. 29, 2022, which is incorporated by reference.

TECHNICAL FIELD

The disclosure generally relates to the field of image processing, and in particular to the automatic segmentation of medical images, such as Computed Tomography (CT) images.

BACKGROUND

In oncology research, accurately segmenting lesions in three dimensions from medical images such as CT scans is crucial for two primary reasons: to extract features for radiomic analysis and to observe lesion growth over time. A lesion is referred to any abnormal tissue or growth, such as tumor, ulcer, or wound. In clinical trials, radiologists use the Response Evaluation Criteria in Solid Tumors (RECIST) guidelines to annotate lesions. This process often includes recording a single diameter or delineating the lesion's two-dimensional shape on the central axial slice of the CT scan, which is referred to as the RECIST image or slice.

Artificial intelligence (AI) and machine learning techniques can be employed to develop a model capable of identifying lesions in medical images. However, training such a machine learning model typically requires a substantial quantity of labeled images, which can be challenging to acquire. Further, in certain instances, a lesion may undergo necrosis. This phenomenon involves the death of cells or tissues within the lesion. The occurrence of necrosis may be caused by various reasons, such as inadequate blood supply, infection, exposure to toxins, or the impact of treatments such as chemotherapy or radiation therapy. As a result of necrosis, the core of the lesion becomes less dense, altering its appearance on medical imaging. This change in appearance poses additional challenges to the application of AI or machine learning in medical imaging analysis.

SUMMARY

Self-supervised learning pretrains deep learning networks with unlabeled data and the pretrained network weights can be transferred for downstream image segmentation task and can improve segmentation performance. Contrastive learning is a state-of-art self-supervised learning method to generate similar semantic representations for positive pairs (augmented views of one image) and dissimilar representations for negative pairs (different images).

Medical images have prior knowledge such as location, shape, and texture of various organs and tissues. Principles described herein embed this prior knowledge and lesion masks (e.g., RECIST annotations) into a contrastive learning framework that improves segmentation performance on necrotic tumors. In addition, a reduced amount of labeled data may be used for downstream supervised training.

Embodiments described herein relate to a system and method of multi-stage training of a machine learning model (e.g., a transformer, convolutional neural network (CNN)). The multi-stage training includes at least the following two stages. During a first stage of pretraining, an encoder is trained to perform contrastive learning from an unlabeled 3D tumor dataset. The unlabeled 3D image dataset contains a plurality of 3D medical images, each of which includes an annotated slice (e.g., a RECIST annotation in 2D) and multiple unannotated slices above and below a lesion identified by the annotated slice. During a second stage of supervised training, the pretrained encoder is fine-tuned in a labeled 2D dataset. The labeled 2D image dataset contains a plurality of 2D labeled medical images, e.g., each of the labeled medical images may have a RECIST annotation.

In some embodiments, the pretraining of the encoder includes augmentation of samples of images from the unlabeled images. In some embodiments, augmenting samples of images includes augmenting positive pairs of images. In some embodiments, augmenting positive pairs includes determining a similarity between a first slice of a lesion and a second slice of the same lesion, and determining whether the similarity exceeds a predetermined threshold T. Responsive to determining that the similarity is greater than the predetermined threshold T, the first slice and the second slice are determined as a positive pair. In some embodiments, the similarity between the first slice and the second slice is determined based on cosine similarity.

In some embodiments, augmenting samples of images includes augmenting masked slices. In some embodiments, the image dataset includes a plurality of slices of a same lesion. The plurality of slices of the same lesion incudes a slice with an annotation that delineates a boundary of the lesion (e.g., a RECIST slice) and remaining slices without an annotation. An area of the lesion on the annotated slice is masked based on the delineated boundary of the lesion. Augmenting masked slices includes masking remaining slices based on distances between points on an unannotated slice of a lesion and a center point of the lesion on a annotated slice (e.g., a RECIST slice) of the same lesion. In some embodiments, the system identifies the center point and radius of the lesion based on the annotated slice, and determines a distance transformation (DT) value between each point on the unannotated slice and the center point of the lesion on the annotated slice. In some embodiments, DT values are normalized to a range of 0 and 1, with 0 representing an edge of the lesion, and 1 representing a center of the lesion. Responsive to determining that the distance transformation value is greater than the predetermined threshold, the point on the unannotated slice is masked.

BRIEF DESCRIPTION OF THE DRAWINGS

The disclosed embodiments have advantages and features which will be more readily apparent from the detailed description, the appended claims, and the accompanying figures (or drawings). A brief introduction of the figures is below.

DETAILED DESCRIPTION

The Figures (FIGS.) and the following description describe certain embodiments by way of illustration only. One skilled in the art will readily recognize from the following description that alternative embodiments of the structures and methods may be employed without departing from the principles described. Reference will now be made to several embodiments, examples of which are illustrated in the accompanying figures. It is noted that wherever practicable similar or like reference numbers are used in the figures to indicate similar or like functionality.

In the field of oncology research, it's essential to segment lesions in medical images (e.g., CT images) three-dimensionally with high accuracy for two main purposes: extracting radiomic analysis features and studying how lesions grow over time. Clinically, during trials, radiologists mark lesions according to the Response Evaluation Criteria in Solid Tumors (RECIST). This marking typically involves noting a single diameter or outlining the lesion's two-dimensional contour on the central axial CT slice, known as the RECIST image or slice. In some embodiments, 2D deep convolutional neural networks (CNNs) may be trained on these 2D RECIST image outlines, for lesion segmentation. This method involves segmenting lesions slice-by-slice and then stacking these 2D slices to create a 3D segmentation, greatly reducing the need for manual 3D outlining. However, this 2D CNN-based approach often falls short in accurately segmenting lung lesions that exhibit necrosis. Note that although embodiments that use RECIST annotations are described for convenience, the disclosed techniques may be used with other forms of image annotation.

Figure 1:
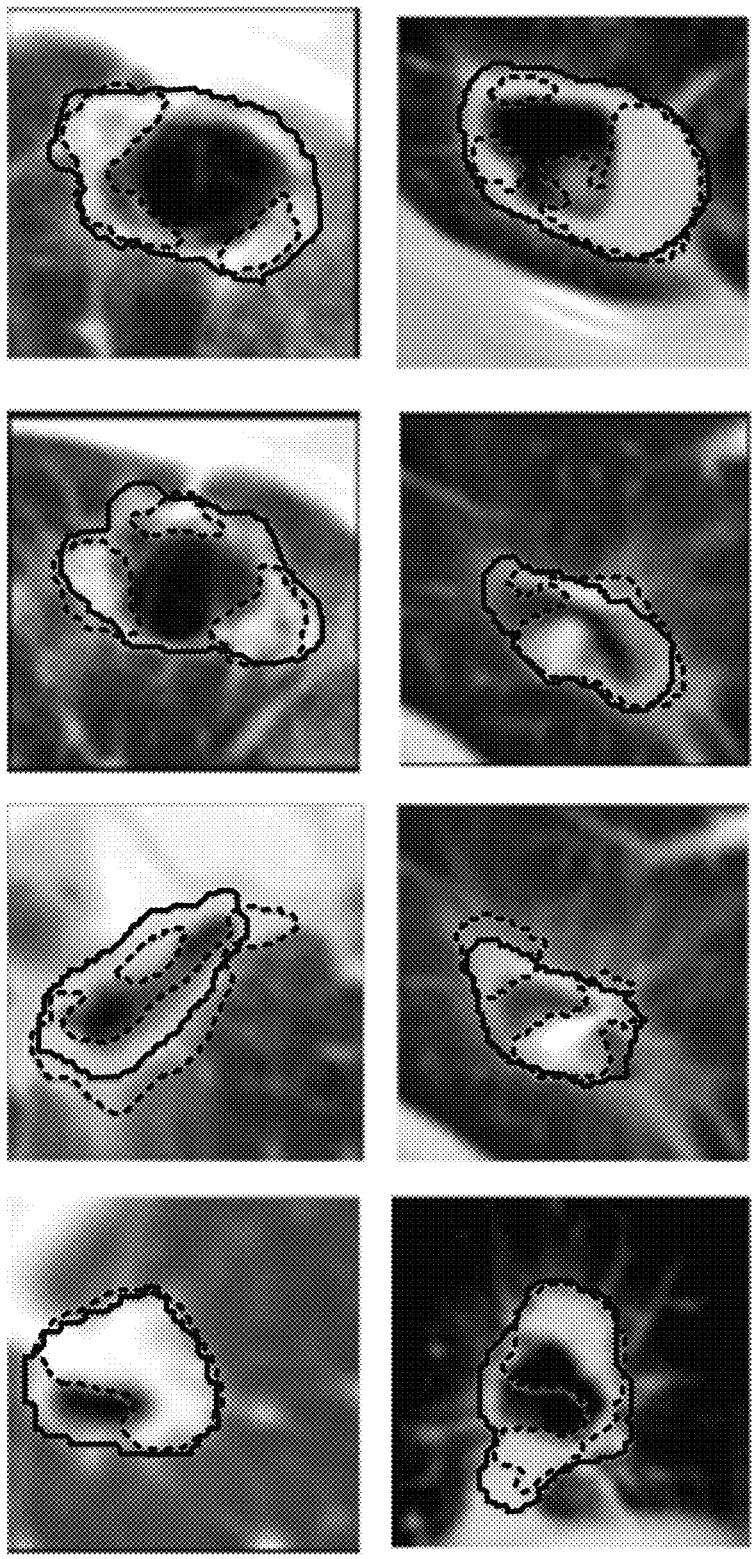
FIG. 1 illustrates example lesions, which are responding to treatment, feature dying lesion cells and thus have less dense cores, posing challenges to traditional machine learning models to accurately delineate the boundaries of the lesions.

FIG. 1 illustrates example lesions, which are responding to treatment, feature dying tumor cells and thus have less dense cores. The issue arises because these 2D CNN models are predominantly trained on lesions with more typical appearances found in the training datasets, leading them to often miss these less dense, necrotic areas in the segmentation process. To address the imbalance in the training data, techniques like re-weighting or re-sampling may be implemented, but they require the time-consuming task of identifying these less common cases.

Embodiments described herein solve the above-described problem by using self-supervised contrastive learning. Self-supervised contrastive learning is a machine-learning technique that may be used to train neural networks to understand and process data without explicit labels. Self-supervised learning uses the input data itself to generate labels or targets for training. In other words, the model learns to predict some aspects of the input data from other aspects of the input data. This is in contrast to supervised learning, where models are trained using human-annotated labels. Contrastive learning is an approach within self-supervised learning to teach the model to distinguish between similar (positive) and dissimilar (negative) pairs of data points. For instance, in the embodiments described herein, two augmented versions of the same medical image (e.g., CT slice) might be considered a positive pair, while two different images (e.g., different CT slices) are treated as a negative pair.

Self-supervised contrastive learning described herein takes advantage of vast amounts of unlabeled data by using augmented image pairs, both positive and/or negative, to develop robust features that are highly relevant to the image domain. This approach can be fine-tuned with a minimal amount of labeled data. Additionally, it has been shown that contrastive learning is particularly effective in managing classes that are less represented, surpassing the robustness of supervised learning methods pre-trained on ImageNet. In light of the abundant amounts of unlabeled 2D CT image slices and the limited availability of labeled 2D RECIST images, the self-supervised contrastive learning method and/or system described herein utilizes RECIST delineations alongside unlabeled images to train models.

Overview of Method

Figure 2:
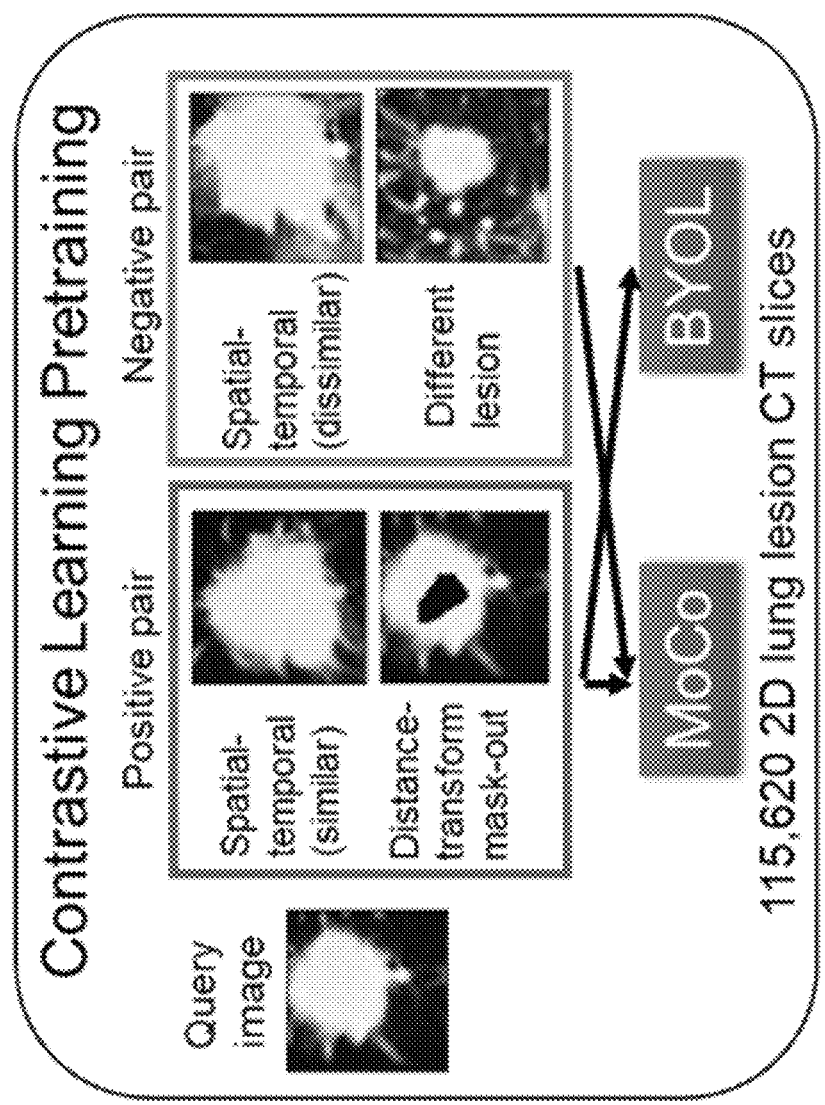
FIG. 2 illustrates a flowchart of performing pretraining using self-supervised contrastive learning in accordance with some embodiments.

FIG. 2 illustrates a flowchart of performing pretraining using self-supervised contrastive learning in accordance with some embodiments. As illustrated, in some embodiments, the system utilizes both spatial and temporal slices of lesions for augmenting positive pairs. The system is able to learn about the anatomical variations throughout the 3D volume and over time. In some embodiments, the system incorporates a distance transform-based mask-out augmentation, which is configured to mimic necrotic lung lesions. This technique aims to enhance the model's effectiveness in handling such lesions, without compromising its performance on typical lung lesions. The CT slices generated via the self-supervised contrastive learning pretraining are then input to a neural network (e.g., MoCo or BYOL network) for training.

Embodiments described herein include a model trained in at least two stages, including (1) a contrastive self-supervised pretraining, and (2) supervised fine-tuning. During a first stage of pretraining, an encoder is trained to perform contrastive learning and cutout volume reconstruction from an unlabeled 3D tumor dataset. The unlabeled 3D image dataset containing a plurality of 3D medical images, each of which includes multiple slices above and below tumors identified by a RECIST annotation in 2D. The pretraining of the encoder includes augmenting positive pairs in the unlabeled 3D tumor dataset. During a second stage of training, the pretrained encoder is fine-tuned in a labeled 2D dataset. The labeled 2D image dataset containing a plurality of 2D medical images, each of which has a RECIST annotation.

Different augmentation methods may be performed during the first stage of training. A first augmentation method includes simulating anatomical variations between a given slice of a lesion and a RECIST slice of the same lesion. In some embodiments, the system determines a similarity between a first slice of a lesion and a second slice of the same lesion, and determines whether the similarity exceeds a predetermined threshold T. In response to determining that the similarity is greater than the predetermined threshold T, the first slice and the second slice are determined as a positive pair. In some embodiments, for a given slice of a lesion, each of remaining slices from the same 3D scan is compared with the given slice to determine a similarity. In some embodiments, the similarity is determined based on cosine similarity.

A second augmentation method includes simulating necrotic anatomy by masking out subregion of lesions based on a distance between a given CT slice and a RECIST slice. The distance is determined based on a technique called distance transform (DT). DT computes a distance of each point on an unlabeled CT image of a lesion and a corresponding RECIST delineation of the lesion. In some embodiments, the distances (also referred to as DT values) are normalized to a range of 0 and 1, with 0 representing an edge of the lesion, and 1 representing a center of the lesion. An area on the unannotated slice with DT values greater than a predetermined threshold $\alpha$ is masked out.

In oncology, 3D segmentation of lesions in CT images is a critical step for various types of studies, such as extracting features for radiomics analysis and calculating 3D volumes of lesions to estimate the lesion growth models. Target tumors are routinely annotated by radiologists following the guidance of Response Evaluation Criteria in Solid Tumors (RECIST), where the diameters and 2D contour labeling of a tumor at the central slice are obtained (hereinafter referred to as RECIST images or RECIST slices). Deep convolutional neural networks (CNN) may be used to segment lesions in 3D based on 2D annotations. These approaches have effectively reduced the demand on manual delineations for creating 2D segmentations. However, the performance of existing models is often inherently biased by most of the lesions showing regular appearance in the training dataset. Therefore, under-represented lesions, such as necrotic lung lesions, are poorly segmented, especially at their hypointense regions. Necrotic lesions are often associated with poor patient prognosis, which is partially caused by under detection.

Further, existing 2D CNN trained on 2D annotated tumor images often cannot learn 3D spatial information. Given a large number of unlabeled 2D images and limited labeled 2D RECIST images, embodiments described herein provide an effective solution for the segmentation of necrotic lung lesions, which improves 3D segmentation performance. In particular, embodiments described herein include a 3D lesion segmentation model trained using a self-supervised pretraining based on contrastive learning. The self-supervised pretraining includes at least one of the following two RECIST-label guided augmentations, namely (1) RECIST-guided distance transform-based mask-out to simulate anatomy of necrotic tumors, and/or (2) RECIST-guided spatial-temporal augmentation to simulate natural anatomical deformations.

Embodiments include pretraining deep learning networks with unlabeled data, and the pretrained network weights can then be transferred for downstream tasks such as image classification, object detection, and image segmentation. Contrastive learning is a self-supervised learning method to generate similar semantic representations for positive pairs (which are augmented views of one image) and dissimilar representations for negative pairs (which are different images).

Embodiments described herein may be implemented on contrastive learning with or without negative cases. For the embodiments using negative cases, the more negative cases that are used, the better the outcome is. To increase the negative cases used, MoCo utilizes a large memory of CPU to store a queue of semantic representations for a large number of negative cases independent of the batch size; simCLR utilizes a large memory of GPU to train with a large batch size. Unlike MoCo or simCLR, which requires a large memory in CPU or GPU to increase the negative cases used, BYOL and SimSiam do not have such a requirement for large memory in CPU or GPU. Instead, BYOL uses an exponential moving average of the target model to generate a semantic representation for an augmented view of the sample; and SimSiam uses a target model with a simple stop gradient.

In some embodiments, contrastive learning not only uses images and the augmented self to construct positive pairs, but also uses additional prior knowledge to identify additional positive pairs. The additional prior knowledge may include (but is not limited to) prior knowledge of imaging artifacts. For example, prostate ultrasound images could suffer from low image quality and shadow artifacts. Prostate ultrasound images may be perturbed in an input space and feature space to simulate shadow artifacts. The network may be encouraged to learn consistent feature representations between the normal images and perturbed images, which may help prostate segmentation with a reduced amount of labeled data.

In some embodiments, spatial-temporal contrastive learning may be implemented to learn from video representations. In particular, temporal augmentation is performed by selecting two clips from a same video and selecting closer clips with higher probabilities. Spatial augmentation is performed by ensuring spatial consistency among frames in a same clip. In 3D medical images, prior knowledge, such as the location and shape of tumors, allows tumor tracking across multiple 3D slices. It is proven that spatial-temporal contrastive learning outperforms ImageNet supervised pretraining by 15.7% and simCLR unsupervised pretraining by 18.8% on Kinetics-600 dataset.

Additionally, in 4D medical images, tumor meta information allows tumor tracking across longitudinal scans. In contrastive learning, the slices from the same tumors across longitudinal scans could also form positive pairs. However, some of these positive pairs are weak because the shape of a tumor may change drastically between slices that are spatially distant or distant in time. To deal with such weak information, self-paced contrastive learning may be implemented to let the network learn from more confident positive pairs at first and less confident pairs later.

In some embodiments, self-supervised contrastive learning utilizes tumor spatial and temporal slices with corresponding RECIST annotations for constructing anatomical positive pairs. In some embodiments, self-supervised contrastive learning uses RECIST annotations and distance transform-based mask-out to generate synthetic necrotic tumors as positive pairs in contrastive learning, aiming to expose the network to more necrotic tumors and improve the segmentation performance on necrotic tumors. A comprehensive ablation study is conducted to evaluate the results of the contrastive learning and proposed augmentation methods described herein. A labeled data efficiency study is also performed to demonstrate the benefit of using less labeled data. Results demonstrate a substantial improvement of segmentation accuracy on necrotic lung lesions without sacrificing the performance on other lung lesions with regular appearance compared to models trained with or without using existing contrastive learning methods.

For the contrastive pretraining, a large number of images (e.g., 115,620 images) from a large number of tumors (e.g., 18,648 tumors), including RECIST slices and non-RECIST slices above and below the RECIST slices, are used. For supervised fine-tuning, a smaller number of slices (e.g., 5,309 slices) and a smaller number of RECIST slices (e.g., 395 slices) with 2D deliberations are used for training and validation, respectively. In some embodiments, three test datasets are used for testing. The first includes a first number (e.g., 250) labeled 3D lung tumors, a second set includes a second number (e.g., 135) DeepLesion 3D lung tumors, and a third set includes a third number (e.g., 96) RECIST slices of necrotic lung tumors. All three test sets are not seen in the training and validation process.

In some embodiments, a machine learning model trained using the principles described herein is a Scale-Invariant and Boundary-Aware deep neural network (hereinafter also referred to as SiBA-net). An example SiBA-net is further described in U.S. Pat. No. 11,232,572, issued Jan. 25, 2022, which is incorporated by reference. In some embodiments, a machine learning model trained using the principles described herein is a Swin transformer-based machine-learning models. An example Swin transformer-based machine-learning model is further described in U.S. application Ser. No. 18/504,075, filed Nov. 7, 2023, which is also incorporated by reference.

Example Systems

Figure 3:
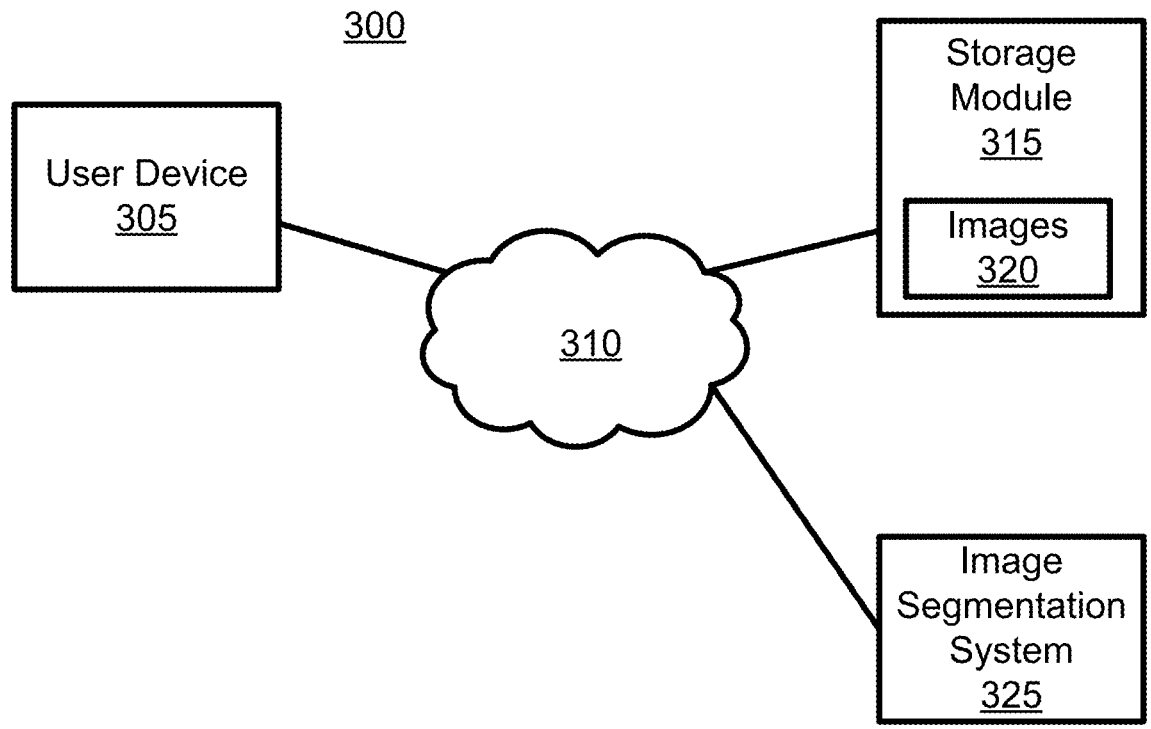
FIG. 3 illustrates a system environment suitable for training the machine-learning model and/or providing the trained machine-learning model for image segmentation in accordance with some embodiments.

FIG. 3 illustrates one embodiment of a system environment 300 suitable for training the machine-learning model and/or providing the trained machine-learning model for image segmentation. In the embodiment shown, the environment 300 includes a user device 305, a network 310, a storage module 315, and an image segmentation system 325. In other embodiments, the system environment 300 includes different and/or additional elements. In addition, the functions may be distributed among the elements in a different manner than described.

The user device 305 is one or more computing devices capable of receiving user input as well as transmitting and/or receiving data via a network 310. In one embodiment, a user device 305 is a computer system, such as a desktop or a laptop computer. Alternatively, a user device 305 may be a device having computer functionality, such as a personal digital assistant (PDA), a mobile telephone, a smartphone, or another suitable device. A user device 305 is configured to communicate via the network 310. The user device 305 may execute an application allowing a user of the user device 305 to interact with the image segmentation system 325 via a user interface. For example, a web browser application may enable interaction between the user device 305 and the image segmentation system 325 via the network 310, or a graphical user interface may be provided as part of a software application published by the image segmentation system 325 and installed on the user device 305. Alternatively, a user device 305 interacts with the image segmentation system 325 through an application programming interface (API) running on a native operating system of the user device 305, such as IOS® or ANDROID™.

The storage module 315 is one or more machine-readable media that store images 320. The storage module 315 may receive and store images 320 from a user device 305, the image segmentation system 325, third-party databases, and the like. In some embodiments, images are computed tomography (CT) images taken of one or more subjects. The images may include lesions, such as lung lesions, liver tumors, mediastinal lesions, subcutaneous lesions, and abdominal lesions. The images may also include enlarged lymph nodes and the like. Images taken consecutively may have spatial dependence. For example, consecutive images may correspond to a set of CT images of a single subject (e.g., CT slices captured along the axial direction of a lesion). Images may correspond to "center slices" and/or "edge slices." Center slices are CT images that have been taken where the lesion looks largest along the axial direction of the lesion. Edge slices are additional CT images of lesions taken at additional locations along the axial direction of the lesions. The storage module 315 may store images used for training, validation, and testing of the image segmentation system 325. A portion of these images may include manual delineations, such as center slices that have been manually delineated to include a single diameter measurement. A portion of these images may include manual delineations at center slices and edge slices that have been manually delineated. An additional portion of these images may not include manual delineations, such as edge slices, that are segmented and refined during inference. In one embodiment, a module with similar or identical functionality to the storage module 315 is integrated into the image segmentation system 325.

The image segmentation system 325 segments CT images to generate 3D segmentations from 2D images (which are also referred to as "slices") and 3D images (which are also referred to as "volumes"). In some embodiments, the image segmentation system 325 uses a SiBa-net. In some embodiments, the image segmentation system 325 uses a Swin transformer-based network. Various embodiments of the image segmentation system 325 are described in greater detail below, with reference to FIGS. 4 through 13.

The user device 305, storage module 315, and image segmentation system 325 are configured to communicate via a network 310, which may include any combination of local area and/or wide area networks, using both wired and/or wireless communication systems. In one embodiment, a network 310 uses standard communications technologies and/or protocols. For example, a network 310 includes communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 310 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 310 may be represented using any suitable format, such as hypertext markup language (HTML) or extensible markup language (XML). In some embodiments, all or some of the communication links of a network 310 may be encrypted using any suitable technique or techniques.

Figure 4:
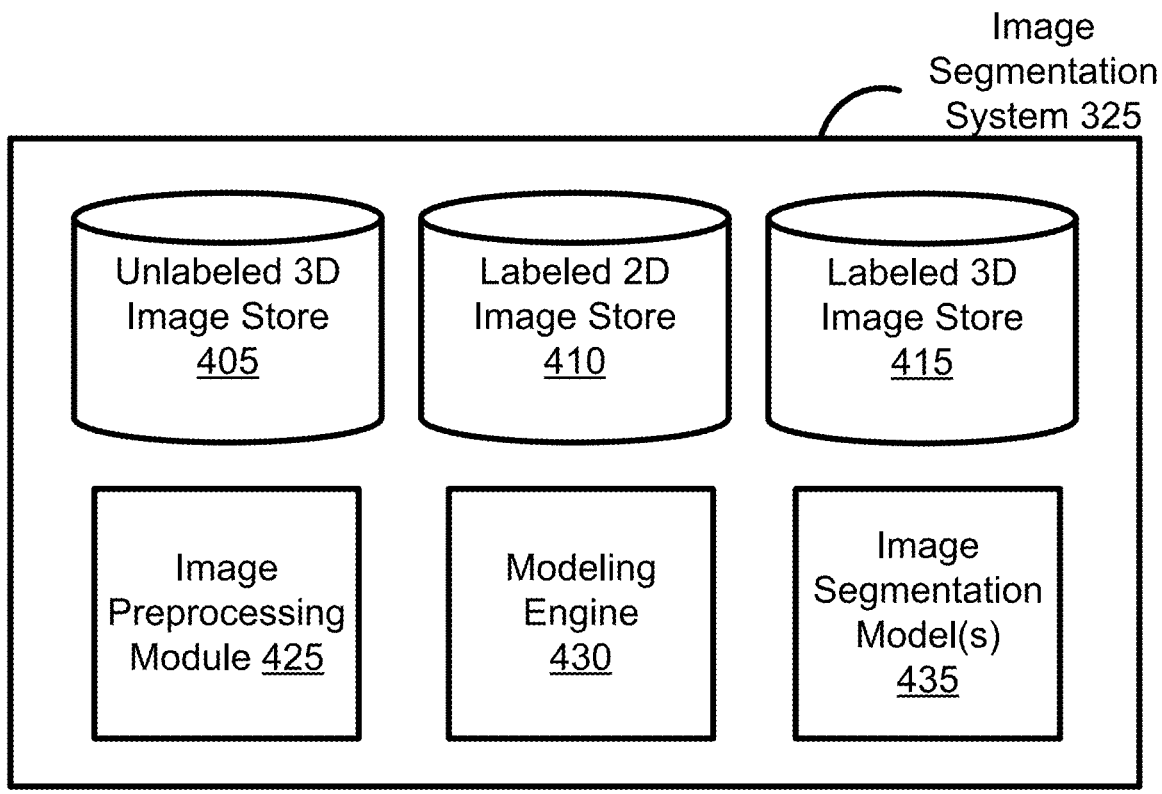
FIG. 4 illustrates an image segmentation system of FIG. 3 in accordance with some embodiments.

FIG. 4 shows one embodiment of the image segmentation system 325 of FIG. 3. In the embodiment shown, the image segmentation system 325 includes an unlabeled 3D image store 405, a labeled 2D image store 410, a labeled 3D image store 415, an image preprocessing module 425, a modeling engine 430, and trained image segmentation model(s) 435. In other embodiments, the image segmentation system 325 includes different and/or additional elements. In addition, the functions may be distributed among the elements in a different manner than described.

The unlabeled 3D image store 405 contains 3D images, each of which includes multiple slices above and below tumors identified by RECIST annotation in 2D. The labeled 2D image store 410 contains labeled 2D images, each of which is with a RECIST annotation. The labeled 3D image store 415 contains labeled 3D images. The boundaries of lesions (such as tumors) in each of the labeled 3D images are annotated. The labeled 2D or 3D images may be obtained from CT slices of lesions that have been captured along an axis of the lesion. The number of slices captured for a single lesion and slice thickness may vary. For example, a set of 2D images or a 3D image may include or be derived from CT slices with a thickness of 1 mm or less, 5 mm or less, 10 mm or less, 15 mm or less, and the like.

Example Embodiments of Preprocessing of Images

In some embodiments, the image preprocessing module 425 is configured to preprocess images before training or segmentation. Preprocessing may include cropping a region of interest on the image to a bounding box. The edges of the bounding box may correspond to a dimension of the subject. For example, each edge of the bounding box may be a multiple of the lesion's longest diameter (e.g., one, two, three, or five times the longest diameter). Preprocessing may also include modifying the intensity of each image. For example, the intensity may be converted into Hounsfield units using various linear transformation parameters (e.g., linear transform parameters recorded in Digital Imaging and Communications in Medicine (DICOM) header). The dynamic range of the intensity may then be shifted and/or cut-off at zero such that all intensity values are non-negative. Further, the intensity may be normalized such that the intensity values range from zero to unity. In this way, the relative intensity changes between voxels are preserved.

In some embodiments, during different stages of training, the image preprocessing module 425 performs different preprocessing to the image datasets stored in image stores 405, 410, and/or 415. For example, in some embodiments, during the first stage, 3D image dataset with RECIST annotations (which may be stored in image store 405) is preprocessed. Each RECIST annotation is a labeled central slice of a 3D lesion volume where the lesion appears to have a longest diameter d. The image preprocessing module 425 is configured to crop the 3D lesion volume by 1.5d×1.5d× 1.5d in x, y, z dimensions with the RECIST annotation at the center of the cropped 3D volume. In some embodiments, the image preprocessing module 425 further resamples the cropped 3D volume to isotropic resolution of 0.75 mm×0.75 mm×0.75 mm. For contrastive learning, all the 2D images from 3D volumes are used for pretraining. For downstream segmentation, the RECIST images and corresponding resampled RECIST annotations are used for supervised training.

In some embodiments, during the second stage, 2D image dataset with RECIST annotations (which may be stored in image store 410) is preprocessed. Each 2D image is a annotated slice having a longest diameter d. The image preprocessing module 425 is configured to crop the 2D image by 1.5 d×1.5 d with RECIST annotation at the center. Similar to the 3D image preprocessing described above, in some embodiments, the image preprocessing module 425 further resamples the cropped 2D image to isotropic resolution of 0.75 mm×0.75 mm. In some embodiments, the image preprocessing module 425 also zero-shift and normalize the resampled and cropped 2D image. In some embodiments, the image preprocessing module 425 further zero-pads/crops the boundary of the 2D image, causing the 2D image to have a size of 128×128.

In some embodiments, during the second stage, labeled 3D images (which may be stored in image store 415) are preprocessed. Each labeled 3D image includes a lesion having a largest diameter d. Similar to the preprocessing of the unlabeled 3D images and/or labeled 2D images, the image preprocessing module 425 is configured to crop each labeled 3D image by 1.5 d×1.5 d×1.5 d. In some embodiments, the image preprocessing module 425 also resamples the cropped 3D image to isotropic resolution of 0.75 mm×0.75 mm×0.75 mm. In some embodiments, the image preprocessing module 425 also zero-shift and normalize the resampled and cropped 3D image, and/or zero pads the boundary of the 3D image, causing the 3D image to have a size of 128×128×64.

In some embodiments, the preprocessed images are then split into multiple subsets for training, validation, and/or testing. In some embodiments, for better computational efficiency, the unlabeled and/or labeled 3D images of the first stage and/or second stage may be resized to 64×64×32, and labeled 2D images of the second stage may be resized to 64×64.

Example Embodiments of Contrastive Learning With Augmentation

In addition to the regular preprocessing methods, such as random cropping, brightness and contrast change, rotation, and flipping, two augmentation methods are implemented for construction of positive pairs. First, multiple positive pairs are identified for each slice based on the following spatial-temporal rule: for one slice in the lesion, the slices from a same lesion across all longitudinal scans is identified as positive pairs if normalized cross correlation (NCC) similarity in RECIST window is greater than T. In particular, for two sets of slices, each including CT images and a corresponding RECIST annotations from a central slice of two tumors, two central slices are cropped to a tight bounding box around RECIST annotations, and resized to 112× 112. The system then calculates normalized cross correlation (NCC) between the two resized cropped images. The system varies T in a range between 0.1-0.9 with a step size of 0.1. Unlike original MoCo, which has one queue to store semantic representations of images, the system uses two additional queues for tumor information, and the resized cropped images for online NCC calculations.

Figure 5:
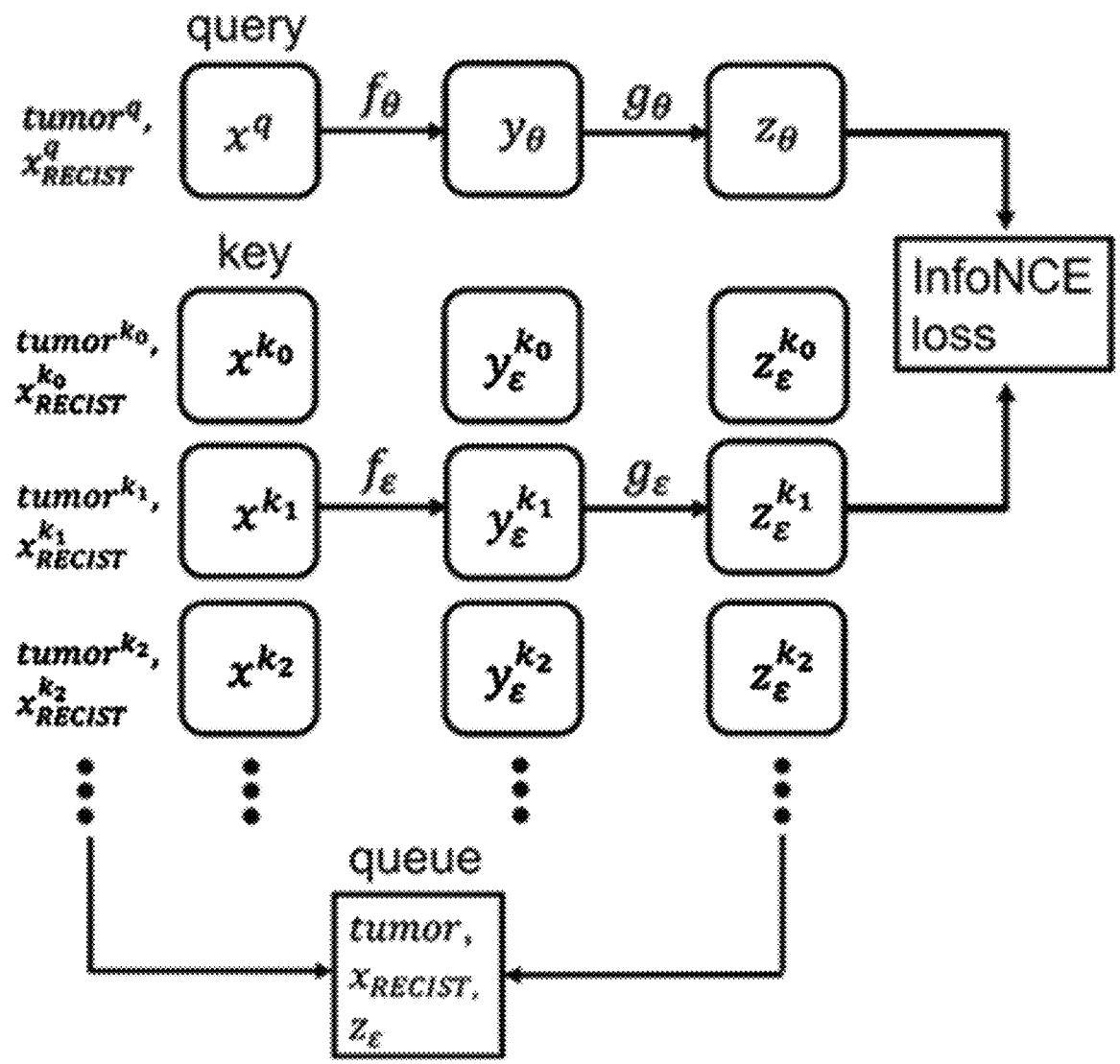
FIG. 5 illustrates an example workflow of RECIST-guided MoCo in accordance with some embodiments.

FIG. 5 illustrates an example workflow 500 of RECIST-guided MoCo. In FIG. 5, $f_\theta$ is the encoder, $g_\theta$ is the multi-layer perceptron (MLP) projector, $f_\epsilon$ is the momentum encoder, $g_\varepsilon$ is the momentum MLP projector. x is image, y and z are vectorized semantic representations; tumor is the tumor identifier consists of trial number, site number, patient number, and tumor ID, which is unique to each tumor; $x_{RECIST}$ is the resized cropped images according to RECIST annotation. For one query image $x^q$, the positive pair should be from the same tumor image identified by $tumor^{k_0}$ and $tumor^{k_1}$ from either spatial or longitudinal images, and should have an NCC calculated by $x_{RECIST}^k$ greater than the threshold T identified by $x_{RECIST}^{k_1}$. $k_0$ and $k_2$ are example negative pairs while $k_1$ is a positive pair.

For a query image, a positive pair is identified from images of a same tumor from either spatial or longitudinal images, and an NCC is calculated based on $x_{RECIST}^k$ greater than the threshold T. Since there may be multiple positive pairs for a single image, the following modified InfoNCE loss may be used:

$$L = -\log \frac{\sum \exp(z_\theta \cdot z_\varepsilon^{k_+}/\tau)}{\sum \exp(z_\theta \cdot z_\varepsilon^{k_+}/\tau + z_\theta \cdot z_\varepsilon^{k_-}/\tau)} \quad (1)$$

where $z_\theta$ is the query embedding, $z_\varepsilon^{k_+}$ and $z_\varepsilon^{k_-}$ are the embeddings from positive and negative pairs, respectively, $\tau$ is a temperature hyperparameter set as 0.995, and $\varepsilon = m\varepsilon + (1-m)\theta$ with m=0.995.

Figure 6:
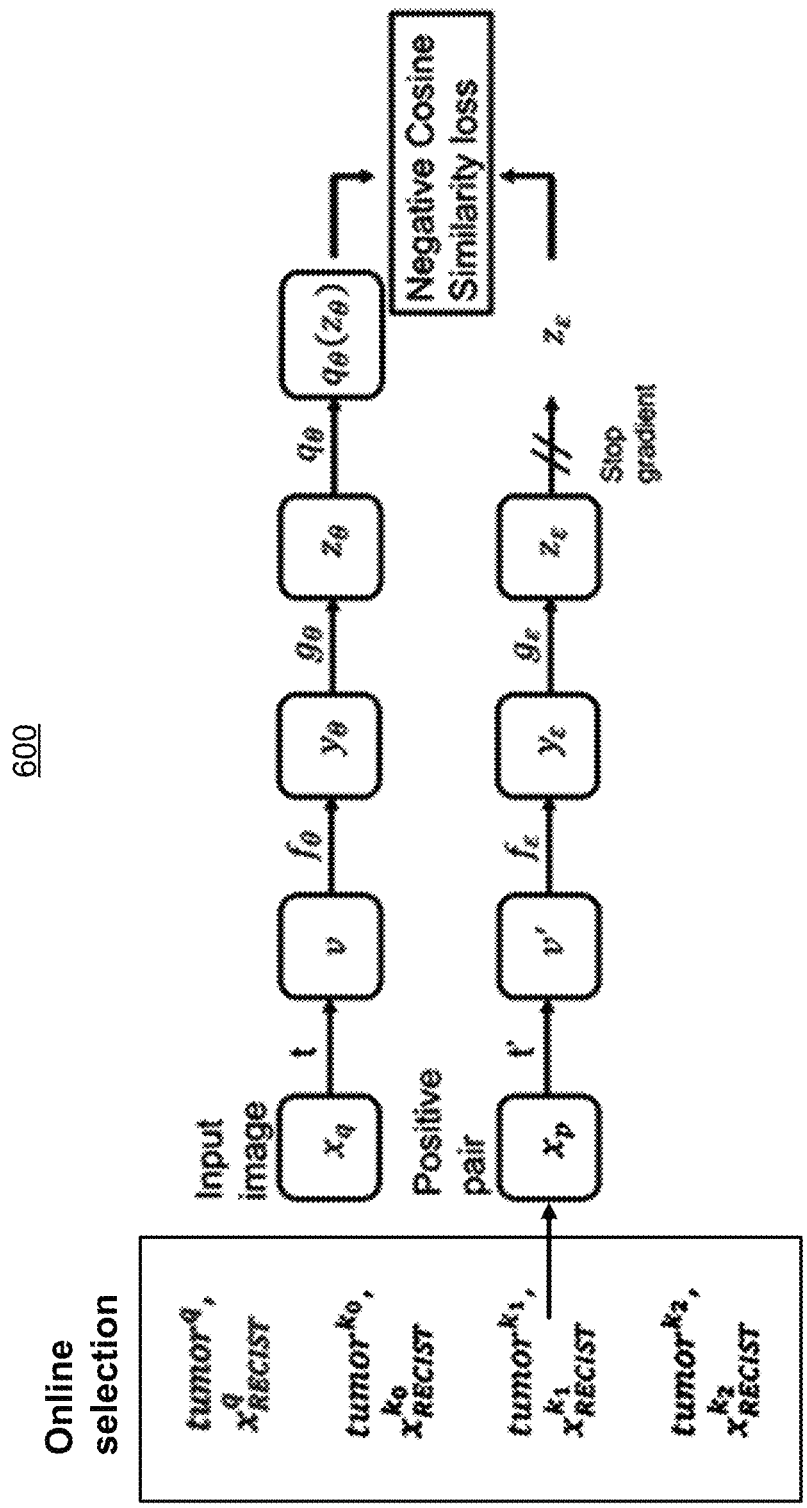
FIG. 6 illustrates an example workflow of RECIST-guided BYOL in accordance with some embodiments.

FIG. 6 illustrates an example workflow 600 of RECIST-guided BYOL. For a query image in BYOL, the system selects one positive pair online from the positive pair pool. The positive pairs pool includes the augmented input itself and other images from the same tumor within current mini-batch that has NCC>T. Here, $q_\theta$ is used as a predictor. The following negative cosine similarity loss may be used:

$$L = -\log \frac{q_\theta(z_\theta) \cdot z_\varepsilon^{k_+}}{\|q_\theta(z_\theta)\|_2 \cdot \|z_\varepsilon^{k_+}\|_2} \quad (2)$$

Further, given one CT image and RECIST annotation from the central slice of the tumor, the system performs distance transform (DDT) on the RECIST annotation mask, normalizes the DT score to 0-1, and mask out the central area of the CT image that has DT score>threshold $\alpha$ and with a probability of 0.6. Threshold $\alpha$ is determined by the distance between the image and the central RECIST slice and the diameter of the tumor measured from RECIST slice as shown in the following equation:

$$\alpha = 0.5 + \frac{|D|}{r} \quad (3)$$

where D is the distance between the current slice and the RECIST slice, and r is the radius of the tumor approximated by averaging the radius along the x and y axis. $\alpha$ is kept in a range between 0.5 and 0.9. As the slices approach the upper and lower end of the tumor, $\alpha$ gets larger, and the masked out region gets smaller.

In addition to conventional data augmentation methods, e.g., rotation, random cropping, and intensity perturbation, the system described herein implement additional novel augmentation methods, namely spatial-temporal augmentation method and distance transform-based mask-out method. In the spatial-temporal augmentation method, multiple positive pairs are identified for each slice using a spatial-temporal rule. For a given slice x, slices from a same lesion on the current 3D scan and across all longitudinal scans are identified as positive pairs if cosine similarity between two resized cropped images $x_{RECIST}^1$ and $x_{RECIST}^2$ is greater than a threshold T. The cosine similarity may be represented by the following equation:

$$\text{Cosine Similarity} = \frac{\langle x_{RECIST}^1, x_{RECIST}^2 \rangle_F}{\|x_{RECIST}^1\|_2 \cdot \|x_{RECIST}^2\|_2} \quad (4)$$

Different learning methods may implement different cosine similarity thresholds T. For example, the training loss of MoCo increases as we increase the cosine similarity threshold. Correspondingly, a cosine similarity threshold of 0.9 introduces more similar negative pairs to the contrastive learning framework. The training loss of BYOL with cosine similarity threshold of 0.1-0.5 converged to a higher loss compared to cosine similarity threshold of 0.6-0.9. And in the range from 0.6 to 0.9, a threshold of 0.7 had the lowest training loss.

In some embodiments, an independent evaluation set including 2D RECIST slices and manual delineations for multiple necrotic lung lesions may be used to optimize the cosine similarity threshold. As shown in Table 1 below, although cosine similarity of 0.9 in MoCo had the highest training loss, it had the best DSC on the evaluation set, manifesting that having challenging negative pairs could benefit the contrastive learning of MoCo. Whereas BYOL didn't use negative pairs, and cosine similarity threshold of 0.7 had the best mean DSC and mean HD. For both BYOL and MoCo, the segmentation dropped significantly with cosine similarity threshold≤0.4.

TABLE 1

|  |  | 0.1 | 0.2 | 0.3 | 0.4 | 0.5 | 0.6 | 0.7 | 0.8 | 0.9 |
|---|---|---|---|---|---|---|---|---|---|---|
| DSC | MoCo | 0.7140 | 0.7161 | 0.7131 | 0.7270 | 0.7283 | 0.7210 | 0.7277 | 0.7400 | 0.7432 |
|  |  | (0.1896) | (0.1882) | (0.1785) | (0.1722) | (0.1791) | (0.1752) | (0.1662) | (0.1695) | (0.1419) |
|  | BYOL | 0.7112 | 0.7122 | 0.7275 | 0.7266 | 0.7184 | 0.7199 | 0.7436 | 0.7350 | 0.7332 |
|  |  | (0.1920) | (0.1832) | (0.1933) | (0.1796) | (0.1841) | (0.1911) | (0.1603) | (0.1764) | (0.1803) |
| HD | MoCo | 14.12 | 13.48 | 14.12 | 13.49 | 12.58 | 13.57 | 13.58 | 12.82 | 12.45 |
|  |  | (8.46) | (7.79) | (7.92) | (7.39) | (7.15) | (7.45) | (6.81) | (6.53) | (6.38) |
|  | BYOL | 15.09 | 14.48 | 14.33 | 14.29 | 13.62 | 13.39 | 13.65 | 13.08 | 13.47 |
|  |  | (9.45) | (10.01) | (11.66) | (10.05) | (9.83) | (8.33) | (9.66) | (9.81) | (9.79) |

Figures 7A, 7B:
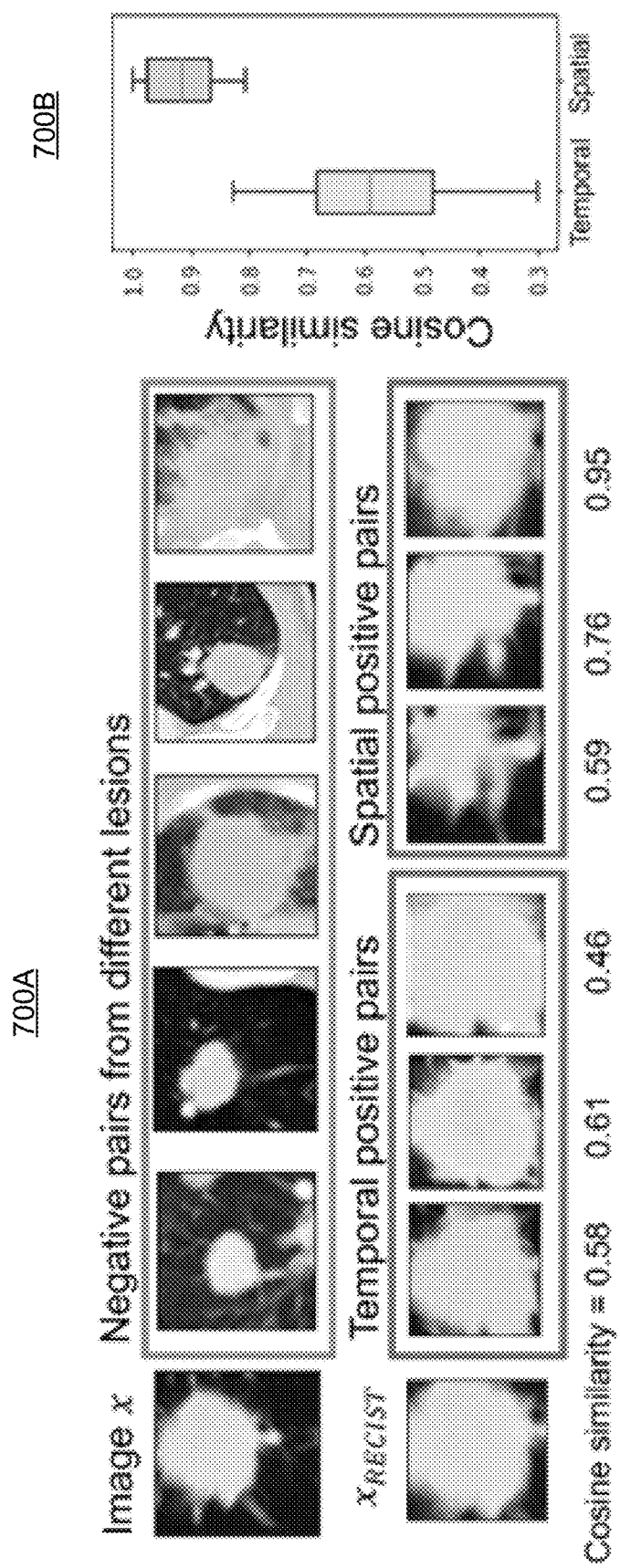
FIG. 7A illustrates examples of temporal positive pairs, spatial positive pairs, and negative pairs in accordance with some embodiments.
FIG. 7B illustrates a box chart of cosine similarity in all candidate positive pairs, with the left box for temporal pairs and the right box for spatial pairs in accordance with some embodiments.

FIG. 7A illustrates examples 700A of temporal positive pairs, spatial positive pairs, and negative pairs. The positive pairs are determined by satisfying at least one of following two criteria: (1) the two tumor images are from the same tumor across longitudinal scans in any spatial slices; and/or (2) the RECIST cropped image have NCC greater than threshold T. The positive pairs satisfy at least one of the above two criteria. The negative pairs are images from different tumors.

FIG. 7B illustrates a box chart 700B of cosine similarity in all candidate positive pairs for $x_{RECIST}$, with the left box for temporal pairs and the right box for spatial pairs. The cosine similarity values in spatial positive pairs are higher tance D being −3 mm, −9 mm, and −15 mm. On the right side of the RECIST slice and RECIST label, there are three slices obtained via distance transformation with distance D being +3 mm, +9 mm, and +15 mm.

The two novel augmentation methods described above are evaluated by conducting an ablation study where augmentations are not applied, applied individually, and applied together. The DSC and HD on the three testing sets are shown in Table 2 below. The special-temporal augmentation and mask-out augmentation are both beneficial for the improvement of necrotic lesion segmentation. Without negative pairs, these strong augmentations introduce more variations in positive pairs, which is beneficial for the success of BYOL.

TABLE 2

|  | Aug1 | Aug2 | DSC | | | HD (mm) | | |
| --- | --- | --- | --- | --- | --- | --- | --- | --- |
|  |  |  | Regular | DeepLesion | Necrotic | Regular | DeepLesion | Necrotic |
| MoCo |  |  | 0.7773* | 0.7802* | 0.6881* | 13.34* | 15.34* | 20.69* |
|  |  |  | (0.1393) | (0.1332) | (0.1527) | (7.26) | (10.19) | (11.62) |
|  | ✓ |  | 0.7837* | 0.7834* | 0.6968* | 13.68* | 15.13* | 21.82* |
|  |  |  | (0.1407) | (0.1153) | (0.1437) | (7.39) | (9.37) | (12.93) |
|  |  | ✓ | 0.7684* | 0.7684* | 0.6797* | 13.46* | 14.85* | 14.37* |
|  |  |  | (0.1544) | (0.1258) | (0.1752) | (7.39) | (9.25) | (6.40) |
|  | ✓ | ✓ | 0.7840 | 0.7950 | 0.7118 | 13.38 | 14.09 | 15.78 |
|  |  |  | (0.1418) | (0.1235) | (0.1489) | (7.30) | (9.12) | (8.09) |
| BYOL |  |  | 0.7379* | 0.6440* | 0.6002* | 16.07* | 21.60* | 20.41* |
|  |  |  | (0.1428) | (0.2040) | (0.1911) | (6.47) | (9.27) | (9.71) |
|  | ✓ |  | 0.7718* | 0.7672* | 0.6454* | 14.24* | 14.34* | 18.57* |
|  |  |  | (0.1396) | (0.1237) | (0.1616) | (7.51) | (7.82) | (9.26) |
|  |  | ✓ | 0.7815* | 0.7660* | 0.6498* | 12.29* | 14.05* | 15.59* |
|  |  |  | (0.1471) | (0.1255) | (0.1696) | (6.68) | (7.59) | (6.68) |
|  | ✓ | ✓ | 0.7701* | 0.7754* | 0.6823* | 13.37* | 14.37* | 17.45* |
|  |  |  | (0.1473) | (0.1172) | (0.1515) | (7.84) | (8.16) | (8.97) | than the temporal pairs, indicating the lesion has more variation between longitudinal scans than the spatial variation in a particular scan. As illustrated in FIG. 7B, cosine similarity is a robust and quantifiable metric for positive pair construction.

In the distance transform-based mask-out method, given one unlabeled CT image and the corresponding RECIST delineation of the lesion, the system performs distance transformation inside a RECIST mask. The system also normalizes α values to a range of [0, 1] with 0 being at a boundary of the lesion, and 1 being at the center of the lesion. The system also masks out the central area of the lesion on the CT image that has distance transform value higher than the threshold α. In some embodiments, threshold α may be determined by the following equation:

$$\alpha \in \left[ 0.5 + \min\left(\frac{|D|}{r}, 0.4\right), 0.9 \right] \quad (5)$$

where D is the distance between the current slice and the RECIST slice, and r is the radius of the lesion. α is kept in the range of [0.5, 0.9]. As the slices approach the upper and lower end of the lesion, α gets larger, and the masked-out region is smaller. In some embodiments, this cropping-based augmentation is applied at a probability of p=0.6.

Figure 8:
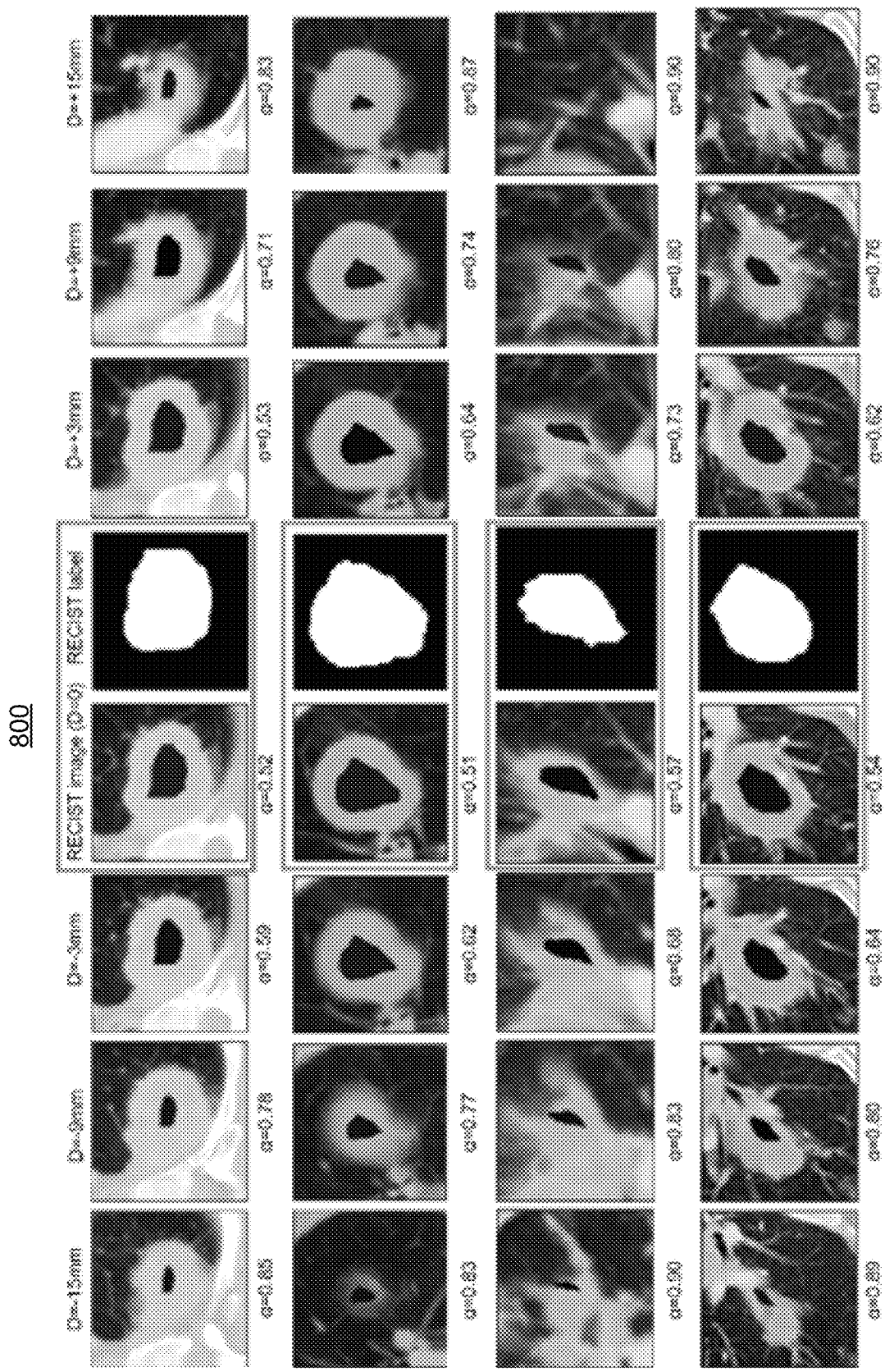
FIG. 8 illustrates examples of images augmented based on the above-described distance transform-based mask-out method in accordance with some embodiments.
Figure 9:
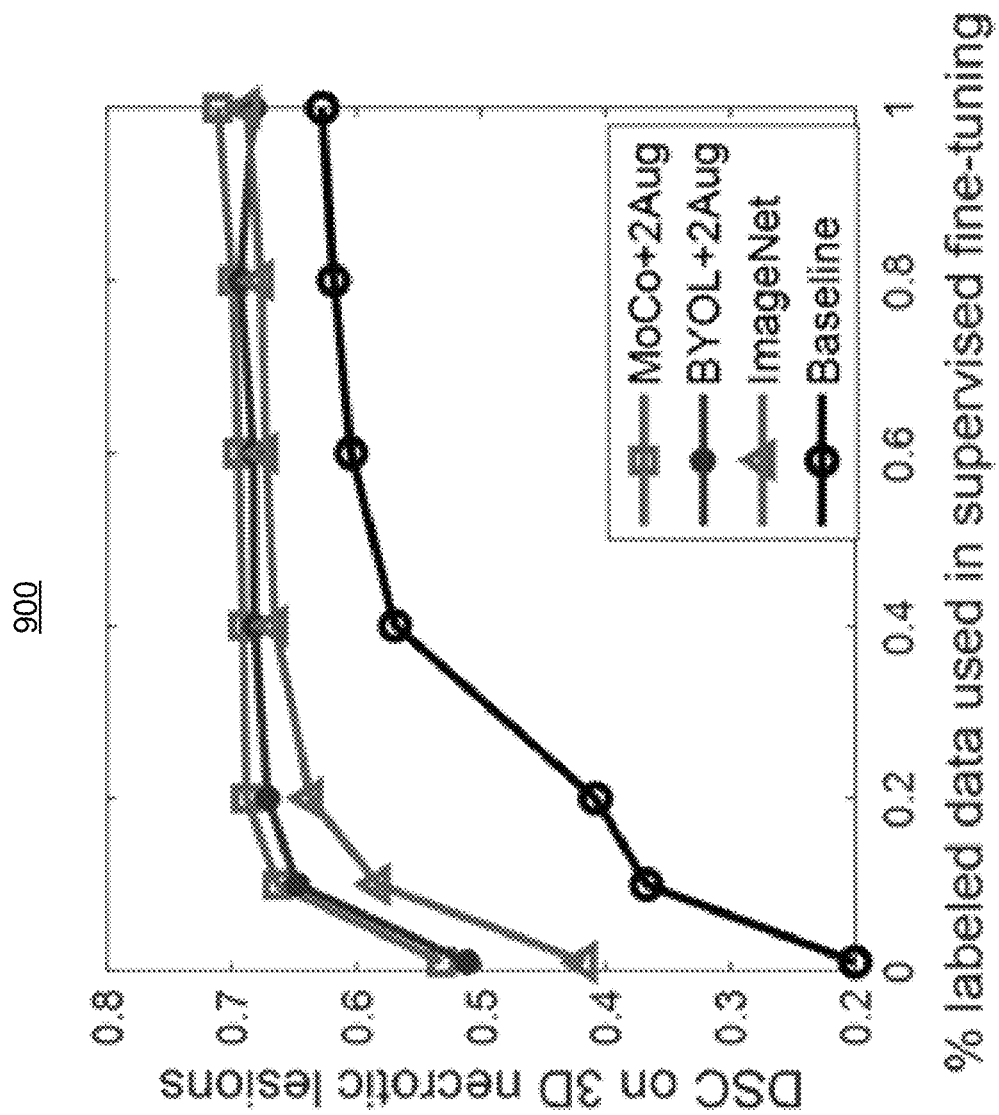
FIG. 9 illustrates a line chart showing performance of self-supervised pretraining with or without the above-described augmentations in accordance with some embodiments.

FIG. 8 illustrates examples 800 of images augmented based on the above-described distance transform-based mask-out method. As illustrated in FIG. 8, two middle columns include RECIST slice and RECIST label. On the left side of the RECIST slice and RECIST label, there are three slices obtained via distance transformation with dis- FIG. 9 illustrates a line chart 900 showing performance of self-supervised pretraining with or without the above-described augmentations. The self-supervised pretraining is able to learn general features and reduce demand on labeled data in downstream tuning. The line chart 900 is generated by varying amount of labeled RECIST slices used in supervised fine-tuning at 1%, 10%, 20%, 40%, 60%, 80%, and 100%, and show the DSC results on the 3D necrotic testing set for Baseline, ImageNet, MoCo+2Aug, and BYOL+ 2Aug. As illustrated, MoCo+2Aug with 10% labels reached better performance than Baseline model trained with 100% labels. Similarly, MoCo+2Aug with 20% labels reached comparable performance as ImageNet pretrained model tuned with 100% labels. BYOL+2Aug shared the same trend as MoCo but performed slightly worse than MoCo in general.

The above-described two self-supervised contrastive learning and two augmentation methods are applied to multiple separate testing datasets (e.g., 250 regular 3D lung lesions from trial, 140 3D lung lesions from public DeepLesion dataset, and 52 necrotic 3D lung lesions from trial). The results of the methods described herein are compared with other methods. In particular, these lesions were segmented using 6 approaches: (1) training from scratch (denoted as "Baseline"), (2) tuning with ImageNet weights (denoted "ImageNet"), (3) tuning with BYOL pretrained weights using the above described two augmentation methods (denoted "BYOL+2Aug"), (4) tuning with MoCo pretrained weights using the above described two augmentation methods (denoted "MoCo+2Aug"), and (5) HRNet with supervised training, and (6) nnUNet with supervised training. The results are shown in Table 3 below.

TABLE 3

|  | DSC | | | HD (mm) | | |
| --- | --- | --- | --- | --- | --- | --- |
|  | Regular | DeepLesion | Necrotic | Regular | DeepLesion | Necrotic |
| Baseline | 0.7534* | 0.7037* | 0.6276* | 14.68* | 17.05* | 19.24* |
|  | (0.1404) | (0.1872) | (0.1739) | (6.35) | (6.90) | (8.86) |
| ImageNet | 0.7780* | 0.7810* | 0.6878* | 13.34* | 14.47* | 19.58* |
|  | (0.1406) | (0.1232) | (0.1510) | (7.34) | (7.97) | (10.57) |
| HRNet | 0.7383* | 0.7759* | 0.6472* | 13.18* | 13.84* | 17.41* |
|  | (0.1661) | (0.1213) | (0.1771) | (6.98) | (7.36) | (7.15) |
| nnUNet | 0.7664* | 0.7654* | 0.6360* | 13.01* | 16.01* | 18.30* |
|  | (0.1438) | (0.1287) | (0.1709) | (6.97) | (9.04) | (8.44) |
| BYOL + 2Aug | 0.7701* | 0.7754* | 0.6823* | 13.37* | 14.37* | 17.45* |
|  | (0.1473) | (0.1172) | (0.1515) | (7.84) | (8.16) | (8.97) |
| MoCo + 2Aug | 0.7840 | 0.7950 | 0.7118 | 13.38 | 14.09 | 15.78 |
|  | (0.1418) | (0.1235) | (0.1489) | (7.30) | (9.12) | (8.09) |

As shown in Table 3 above, in comparison to other methods, the MoCo+2Aug model demonstrated superior performance across all three testing sets, achieving notably higher Dice Similarity Coefficient (DSC) scores, particularly for necrotic lung lesions. This model outperformed others significantly, showing an 8.42% and 2.40% improvement in DSC for 3D necrotic testing sets when compared to the Baseline and ImageNet models, respectively.

Figure 10:
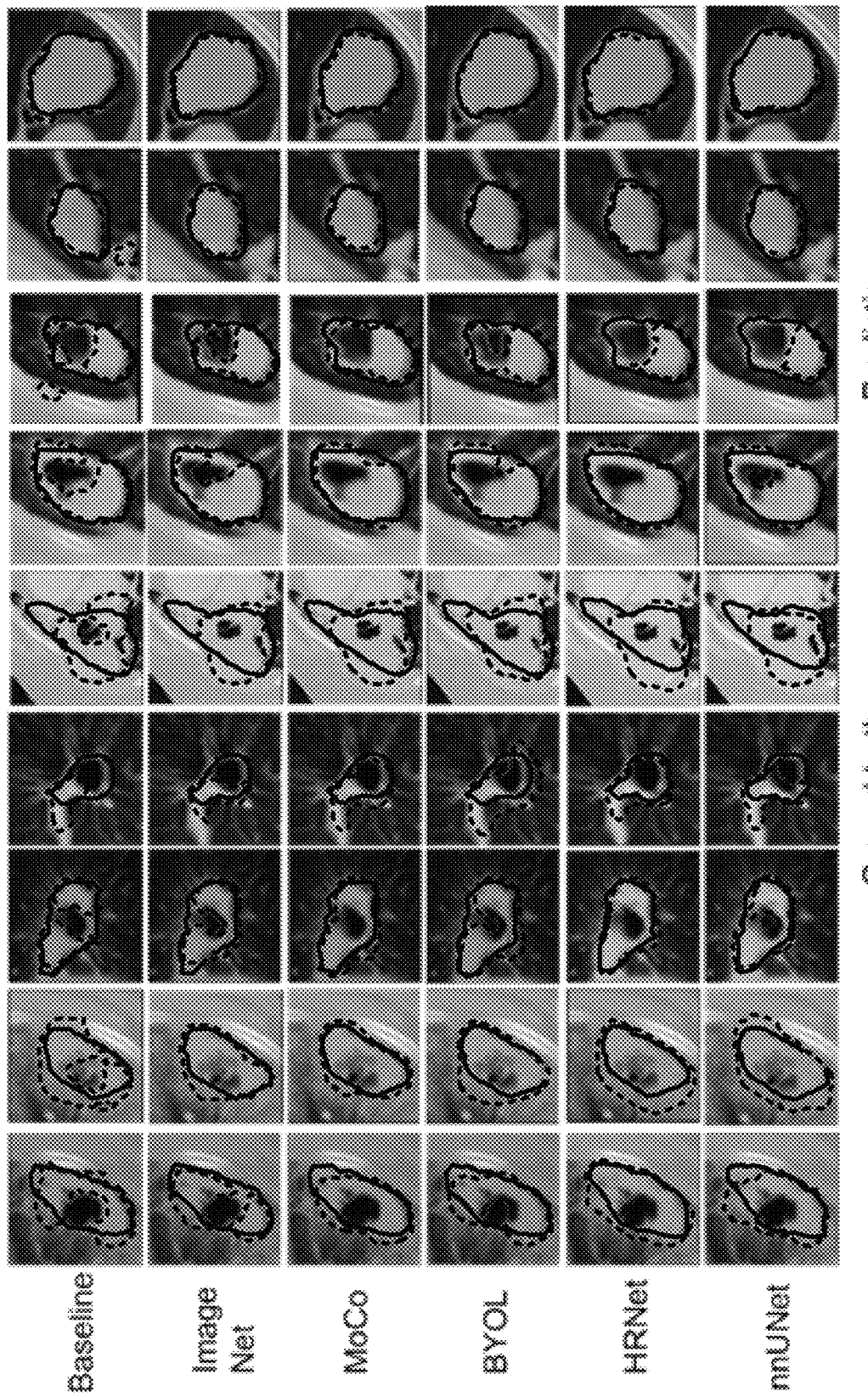
FIG. 10 illustrates a visualization of segmentation results on examples of seven necrotic (left) and 2 regular (right) lung lesions from Baseline model, ImageNet pretrained model, MoCo with two augmentation methods, BYOL with two augmentation methods, HRNet and nnUNet.

FIG. 10 illustrates visualization of segmentation results on examples of 7 necrotic (left) and 2 regular (right) lung lesions from Baseline model, ImageNet pretrained model, Moco with two augmentation methods, BYOL with two augmentation methods, HRNet and nnUNet.

Example Embodiments of Machine-Learning Networks

Figure 11:
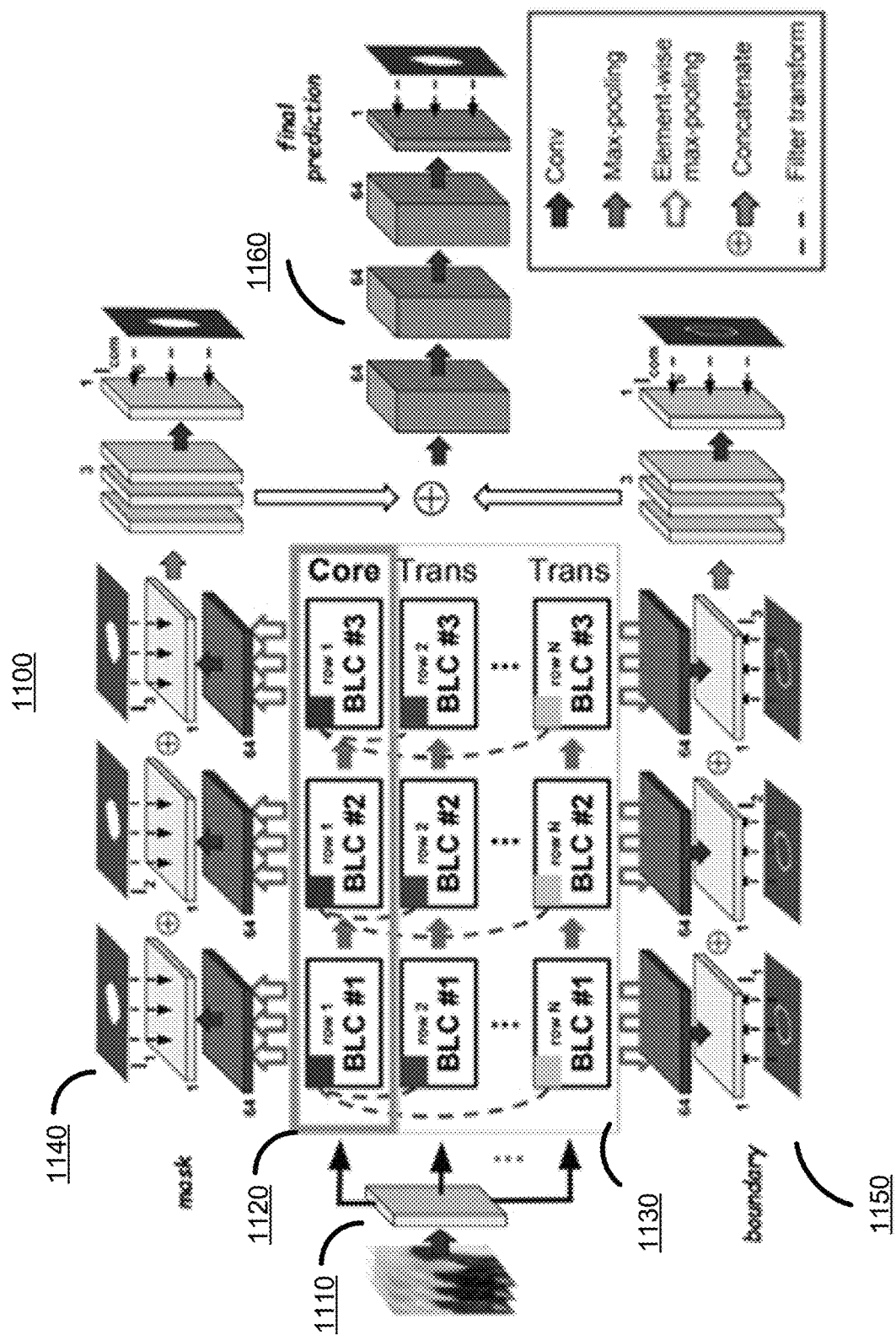
FIG. 11 illustrates an example architecture of a scale-invariant and boundary-aware neural network (also referred to as SIBA-Net) that may be implemented to perform the training described above in accordance with some embodiments.

FIG. 11 illustrates an example architecture of scale-invariant and boundary-aware neural network (also referred to as SIBA-Net) 1100 that may be implemented to perform training described above, in accordance with some embodiments. The image includes multiple rows of pixels. The SIBA-Net 1100 includes an input layer 1110 configured to take an image (e.g., a CT image) as input. The SIBA-Net 1100 also includes a core branch 1120 and multiple transformation branches 1130, each including a series of blocks, BLC #1, BLC #2, and BLC #3 configured to perform contrastive pretraining. The SIBA-Net 1100 also includes two side branches 1140, 1150 configured to perform augmentation to the image. The top branch 1140 is configured to mask-out augmentation. The bottom branch 1150 is configured to perform spatial-temporal augmentation. Outputs of the core branch 1120, transformation branches 1130, and side branches 1140, 1150 are input to a final prediction network 1160 configured to predict lesions based on the image.

Figure 12:
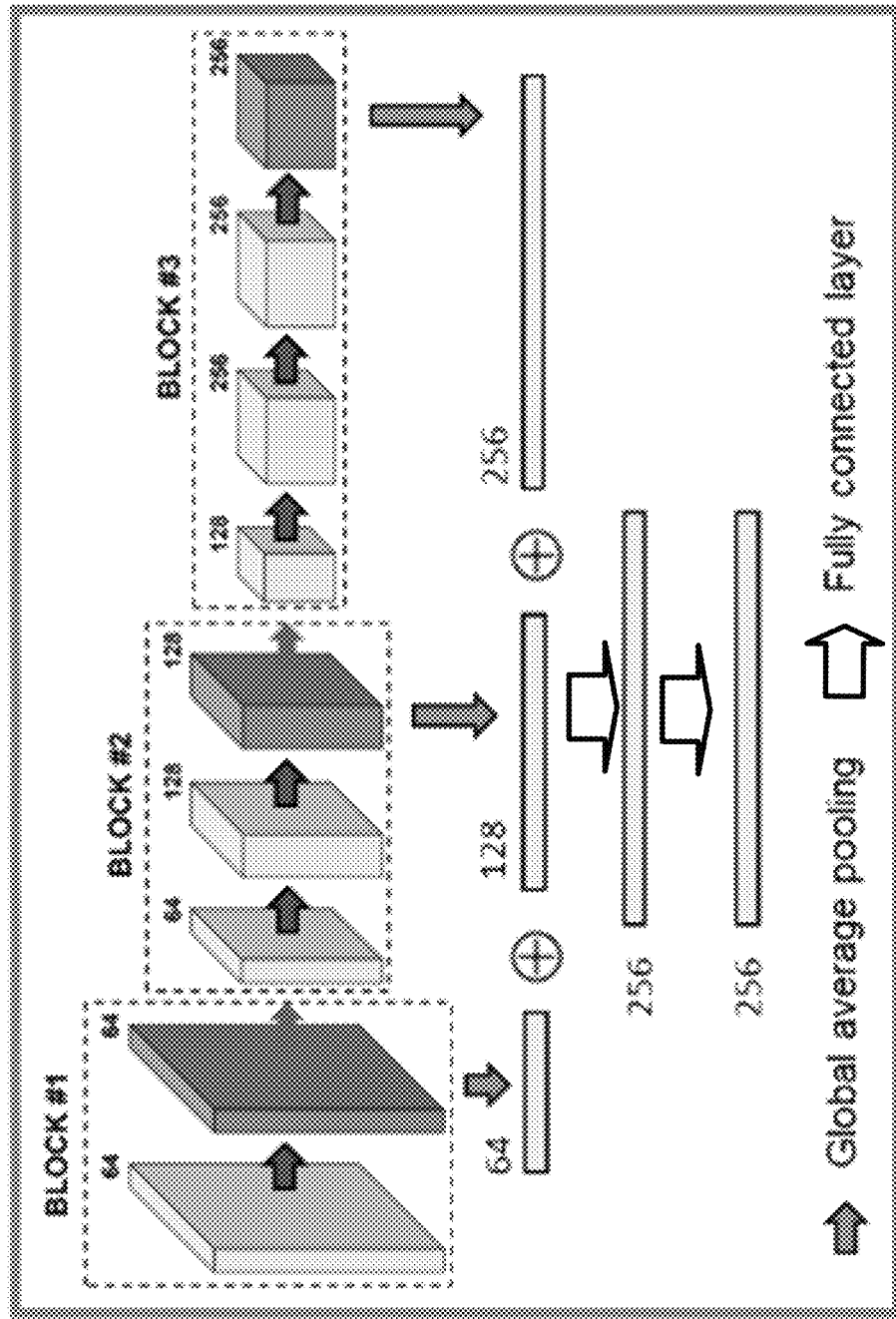
FIG. 12 illustrates an example architecture of contrastive pretraining network that may be implemented to perform contrastive pretraining described above, in accordance with some embodiments.

FIG. 12 illustrates an example architecture of contrastive pretraining network 1200 that may be implemented to perform contrastive pretraining described above, in accordance with some embodiments. The contrastive pretraining network 1200 may correspond to a core branch 1120 of the SIBA-Net of FIG. 11. As illustrated in FIG. 12, the core branch includes three blocks BLOCK #1, BLOCK #2, BLOCK #3. The first block includes two layers, the second block includes three layers, and the third block includes four layers. Global average pooling is performed at each of the three blocks to reduce dimensions. The pooled features are passed to a fully connected layer to combine features.

In some embodiments, the modeling engine 430 is configured to pretrain visual graphic group (VGG) blocks (e.g., the blocks in the core branch 1120 and transformation branches 1130 in FIG. 11, or the network 1200 in FIG. 12) of a SiBA-Net. In some embodiments, global average pooling is performed on the output feature maps from each block, generating vectors of size 64, 128, and 256, respectively. The vectors were concatenated and fed into two multilayer perceptron layers with 256, and 256 as the output dimensions. In some embodiments, the system utilized MoCo queue size of 40,000, MoCo momentum for updating key encoder of 0.999, MoCo softmax temperature of 0.05, mini-batch size of 200, number of epochs of 100, and Adam optimizer with a learning rate of 10-3. The data augmentation for pretraining included distance transform-based mask-out, random cropping, horizontal flipping, random rotation in (0°, 90°, 180°, 270°), and random noise.

In some embodiments, after pretraining via contrastive learning with augmentation, the system then performs supervised fine-tuning. In some embodiments, a SiBA-net is used as a common CNN architecture. For supervised fine-tuning, the system fine-tuned the whole SiBA-Net without freezing any layers, and we used a mini-batch size of 64, a number of epochs of 100, and an Adam optimizer with a learning rate of 10-4. The system may use random cropping for data augmentation in supervised training. Early stopping was applied if the validation loss didn't decrease for 10 epochs. No post-processing is required to be performed.

The experimental data shows that a machine-learning model trained based on the principles described herein outperform many other models trained based on existing machine-learning technologies, such as (but not limited to) ImageNet transfer learning without contrastive learning and/ or with MoCo machine learning algorithms. In particular, the machine learning model trained based on the principles described herein substantially outperforms other models in predictions of necrotic lung lesions.

In some embodiments, the modeling engine 430 is configured to train a Swin transformer-based machine learning model. Since both 2D and 3D images are used for the training, the Swim transformer-based machine learning model is also referred to as a multi-dimension unified Swin transformer (MDU-ST). A Swin transformer encoder in a machine-learning network transforms the input, regardless of its dimensions, to be unified as a 2D linear embedded feature map one dimension matching the number of tokens in the input. The learned feature map after transformer encoding can be decoded to the input shape. This property enables lesion segmentation framework by leveraging (1) unlabeled 3D image datasets, and (2) both rich 2D and limited 3D labeled datasets, alleviating the overfitting issue for a transformer-based model.

Figure 13:
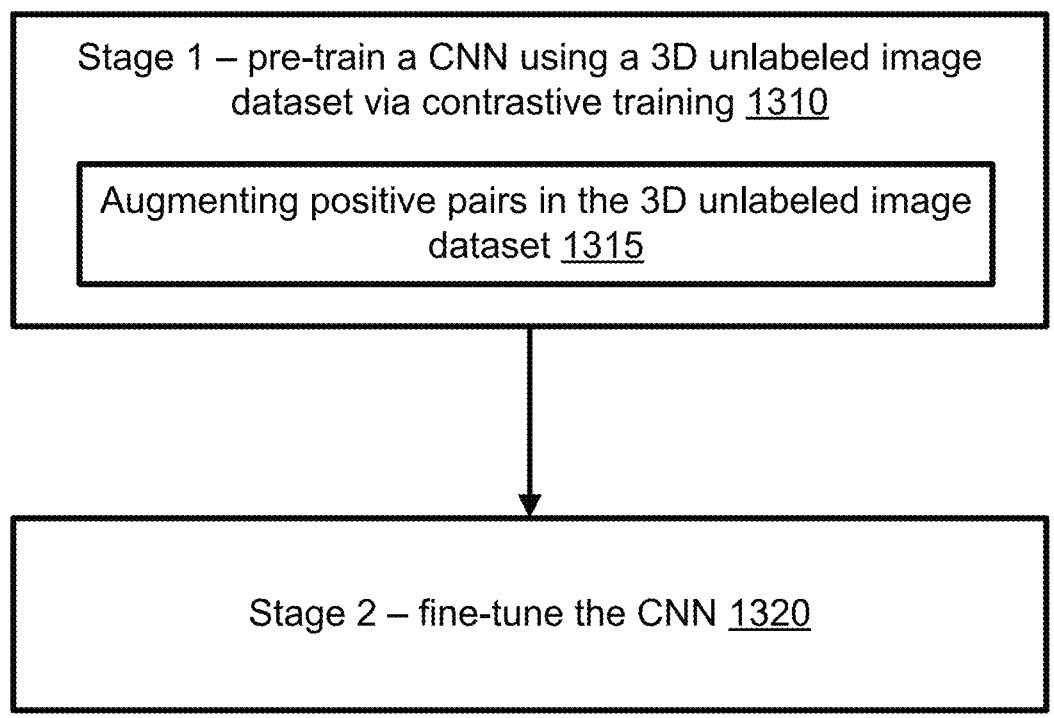
FIG. 13 illustrates a flowchart of a method of training a machine learning model for image segmentation.

FIG. 13 illustrates a flowchart of a method 1300 of training a machine learning model for image segmentation. The machine learning model may be a CNN network, such as a SiBA-net or a transformer-based network. The method 1300 is performed by a computing system, such as an image segmentation system 325 of FIG. 4. The computing system pre-trains 1310 a CNN using a 3D unlabeled image dataset via contrastive training. The unlabeled 3D image dataset containing a plurality of 3D medical images. Each 3D medical image includes an annotated 2D slice and multiple non-annotated 2D slices above and below the annotated 2D slice. The annotated 2D slice includes an annotation that delineates a boundary of a lesion.

Pre-training 1310 the CNN includes augmenting 1315 positive pairs in the 3D unlabeled image dataset. In some embodiments, augmenting positive pairs includes augmenting positive pairs of images based on a similarity between a first slice and a second slice of a same lesion. In some embodiments, the similarity is determined based on cosine similarity. The system determines whether the similarity is greater than a predetermined threshold. Responsive to determining that the similarity is greater than the predetermined threshold, the system determines that the first slice and the second slice are a positive pair. In some embodiments, for a given slice, the system compares each of the remaining slices with the given slice to determine a similarity, and determines whether the given slice and the remaining slice are a positive pair or a negative pair.

The first slice or the second slice may or may not be the annotated slice. The first slice and the second slice may or may not be obtained at a same time (i.e., from a same 3D scan). For example, in some embodiments, the first slice and the second slice may be obtained from a same 3D scan. Alternatively, the first and second slices could be sourced from different 3D scans taken at different times. Consequently, while both slices feature the same lesion, there could be variations due to the lesion's progression over time.

In some embodiments, an area of the lesion on the annotated slice is masked based on the delineated boundary of the lesion. The system is further configured to augments masked slices by masking the remaining slices that are without annotations. In some embodiments, masking a remaining slice is based on distances between points on the remaining slice of the lesion and a center point of the lesion on the annotated slice. In some embodiments, masking a remaining slice includes identifying the center point and a radius of the lesion on the annotated slice, and determining a distance transformation value between a point on the remaining slice and the center point of the lesion on the annotated slice. The system also determines whether the distance transformation value is greater than a predetermined threshold. Responsive to determine that the distance transformation value is greater than the predetermined threshold, the system masks the point on the remaining slice. In some embodiments, this process repeats for each point on the remaining slice, such that an area of the lesion on the remaining slice is masked. In some embodiments, the masking process is performed on each remaining slice to mask out areas of the lesion on the corresponding remaining slice.

The computing system then fine-tunes 1320 the CNN using a labeled 2D dataset. The labeled 2D image dataset contains a plurality of 2D slices of lesions, each of which includes an annotation that delineates a boundary of a corresponding lesion on the slice. In some embodiments, each of the 2D slices in the labeled 2D dataset is a RECIST slice. In some embodiments, the CNN is a SiBA-net. In some embodiments, the CNN is a Swin transformer-based machine-learning network.

Even though the embodiments described herein use CT images with and/or without RECIST annotations, the principle described herein are not limited to CT images and/or RECIST annotations. Other medical images with and/or without annotations under other criteria may be used to train models to delineate other types of lesions via the methods described herein.

Figure 14:
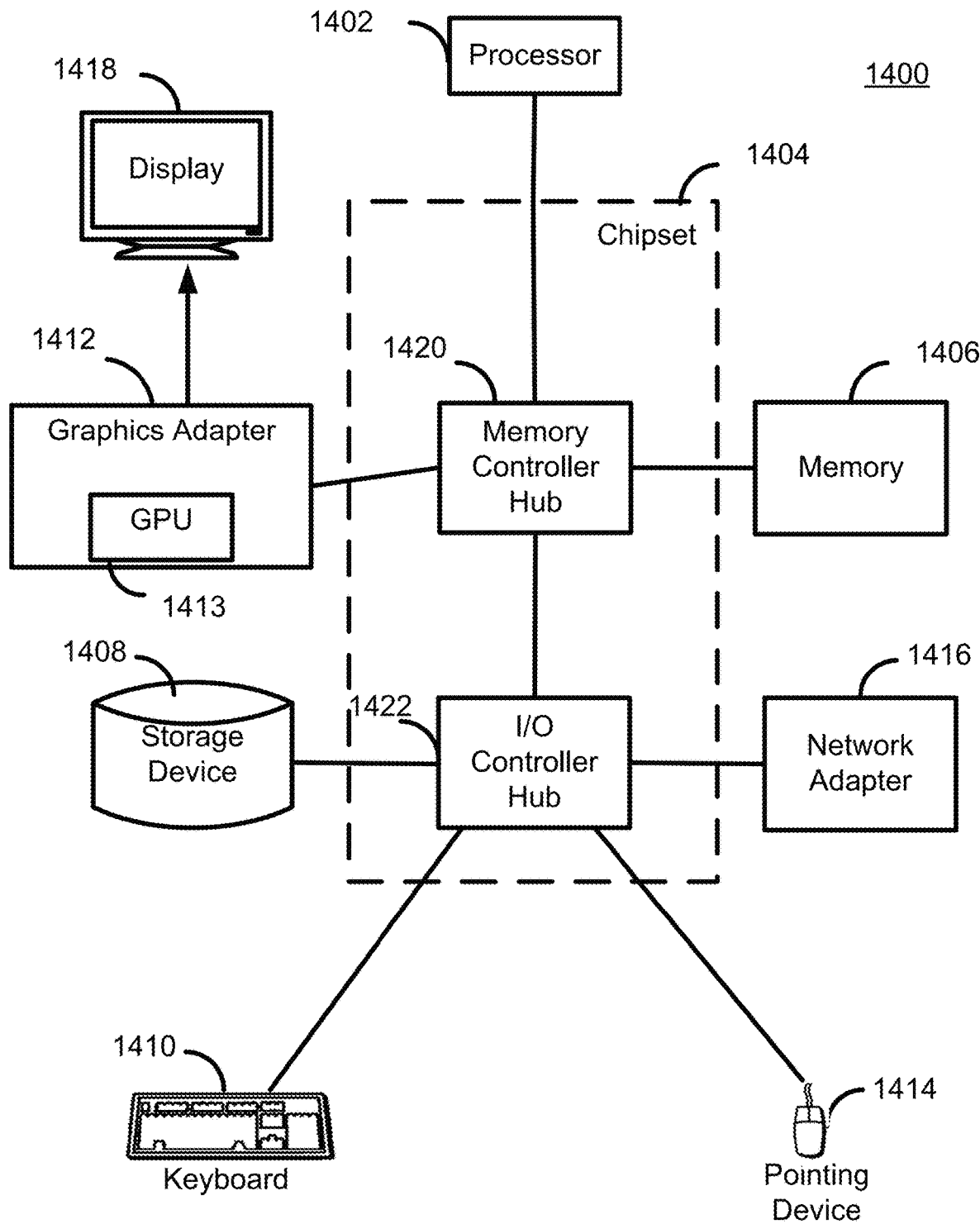
FIG. 14 is a high-level block diagram illustrating an example computer suitable for use in the system environment of FIG. 3.

FIG. 14 is a high-level block diagram illustrating an example computer 1400 suitable for use in the system environment of FIG. 3. The example computer 1400 may be accessible by users via a computer network. For example, the example computer 1400 may be a remote computing system hosted on a cloud platform and/or a virtual machine provided by a cloud service. The example computer 1400 includes at least one processor 1402 coupled to a chipset 1404. The chipset 1404 includes a memory controller hub 1420 and an input/output (I/O) controller hub 1422. A memory 1406 and a graphics adapter 1412, which contains a graphics processing unit (GPU) 1413, are coupled to the memory controller hub 1420, and a display 1418 is coupled to the graphics adapter 1412. A storage device 1408, keyboard 1410, pointing device 1414, and network adapter 1416 are coupled to the I/O controller hub 1422. Other embodiments of the computer 1400 have different architectures.

In the embodiment shown in FIG. 14, the storage device 1408 is a non-transitory computer-readable storage medium such as a hard drive, compact disk read-only memory (CD-ROM), DVD, or a solid-state memory device. The memory 1406 holds instructions and data used by the processor 1402. The pointing device 1414 is a mouse, track ball, touchscreen, or other type of pointing device, and is used in combination with the keyboard 1410 (which may be an on-screen keyboard) to input data into the computer 1400. The graphics adapter 1412 displays images and other information on the display 1418. The network adapter 1416 couples the computer 1400 to one or more computer networks.

The GPU 1413 in the graphics adapter 1412 may be used for other high-performance computation as well as processing graphical data for presentation on the display 1418. In one embodiment, the GPU 1413 is used to process data from the image segmentation system 325, where it is used to accelerate model training, image processing, and image segmentation.

The types of computers used by the entities of FIG. 14 can vary depending upon the embodiment and the processing power required by the entity. For example, the image segmentation system 325 might include a desktop computer to provide the functionality described. Furthermore, the computers can lack some of the components described above, such as keyboards 1410, graphics adapters 1412, and displays 1418.

Additional Considerations

Some portions of above description describe the embodiments in terms of algorithmic processes or operations. These algorithmic descriptions and representations are commonly used by those skilled in the computing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality.

Any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Similarly, use of "a" or "an" preceding an element or component is done merely for convenience. This description should be understood to mean that one or more of the elements or components are present unless it is obvious that it is meant otherwise.

Where values are described as "approximate" or "substantially" (or their derivatives), such values should be construed as accurate +/-10% unless another meaning is apparent from the context. From example, "approximately ten" should be understood to mean "in a range from nine to eleven."

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Upon reading this disclosure, those of skill in the art will appreciate still additional alternative structural and functional designs. Thus, while particular embodiments and applications have been illustrated and described, it is to be understood that the described subject matter is not limited to the precise construction and components disclosed. The scope of protection should be limited only by the following claims.

What is claimed is:

1. A computer-implemented method of training a convolutional neural network (CNN), the method comprising:
   pre-training via contrastive learning, an encoder of the CNN using an unlabeled 3D image dataset, the unlabeled 3D image dataset containing a plurality of 3D medical images, each of which includes an annotated slice and multiple non-annotated 2D slices above and below the annotated slice, the annotated 2D slice including an annotation that delineates a boundary of a lesion, wherein the unlabeled 3D image dataset comprises a plurality of slices of a same lesion, and the plurality of slices of the same lesion comprises a slice with an annotation that delineates a boundary of the lesion and remaining slices without an annotation, and wherein pre-training via contrastive learning further comprises:
      masking an area of the lesion on the annotated slice based on the delineated boundary of the lesion; and
      augmenting masked slices by masking a remaining slice based on distances between points on the remaining slice of the lesion and a center point of the lesion on the annotated slice; and
   fine-tuning the pre-trained encoder using an annotated 2D image dataset, the annotated 2D image dataset containing a plurality of 2D slices of lesions, each of which includes an annotation that delineates a boundary of a corresponding lesion.

2. The computer-implemented method of claim 1, wherein the method further comprising:
   augmenting positive pairs of 2D images based on a similarity between a first slice and a second slice of a same lesion.

3. The computer-implemented method of claim 2, wherein augmenting the positive pairs comprises:
   determining a similarity between the first slice and the second slice;
   determining whether the similarity is greater than a predetermined threshold; and
   responsive to determining that the similarity is greater than the predetermined threshold, determining that the first slice and the second slice are a positive pair.

4. The computer-implemented method of claim 1, wherein masking a remaining slice comprises:
   identifying the center point and a radius of the lesion on the annotated slice;
   determining a distance transformation value between a point on the remaining slice and the center point of the lesion on the annotated slice;
   determining whether the distance transformation value is greater than a predetermined threshold; and
   responsive to determining that the distance transformation value is greater than the predetermined threshold, masking the point on the remaining slice.

5. The computer-implemented method of claim 4, wherein the predetermined threshold is determined based in part on a distance between the non-annotated slice and the annotated slice and a radius of the lesion.

6. The computer-implemented method of claim 4, wherein the distance transformation value is normalized to a range of 0 and 1, with 0 representing an edge of the lesion, and 1 representing a center of the lesion.

7. A non-transitory computer readable storage medium comprising instructions that, for training of a convolutional neural network (CNN) in multiple stages, the instructions, when executed by one or more processors, causing the one or more processors to:
   pre-train via contrastive learning, an encoder of the CNN using an unlabeled 3D image dataset, the unlabeled 3D image dataset containing a plurality of 3D medical images, each of which includes an annotated slice and multiple non-annotated 2D slices above and below the annotated slice, the annotated 2D slice including an annotation that delineates a boundary of a lesion, wherein the unlabeled 3D image dataset comprises a plurality of slices of a same lesion, and the plurality of slices of the same lesion comprises a slice with an annotation that delineates a boundary of the lesion and remaining slices without an annotation, and wherein pre-training via contrastive learning further comprises:
      masking an area of the lesion on the annotated slice based on the delineated boundary of the lesion; and
      augmenting masked slices by masking a remaining slice based on distances between points on the remaining slice of the lesion and a center point of the lesion on the annotated slice; and
   fine-tune the pre-trained encoder using an annotated 2D image dataset, the annotated 2D image dataset containing a plurality of 2D slices of lesions, each of which includes an annotation that delineates a boundary of a corresponding lesion.

8. The non-transitory computer readable storage medium of claim 7, wherein the one or more processors are further caused to:
augment positive pairs of 2D images based on a similarity between a first slice and a second slice of a same lesion.

9. The non-transitory computer readable storage medium of claim 8, wherein augmenting the positive pairs comprises:
determining a similarity between the first slice and the second slice;
determining whether the similarity is greater than a predetermined threshold; and
responsive to determining that the similarity is greater than the predetermined threshold, determining that the first slice and the second slice are a positive pair.

10. The non-transitory computer readable storage medium of claim 8, wherein masking a remaining slice comprises:
identifying the center point and a radius of the lesion on the annotated slice;
determining a distance transformation value between a point on the remaining slice and the center point of the lesion on the annotated slice;
determining whether the distance transformation value is greater than a predetermined threshold; and
responsive to determining that the distance transformation value is greater than the predetermined threshold, masking the point on the remaining slice.

11. The non-transitory computer readable storage medium of claim 10, wherein the predetermined threshold is determined based in part on a distance between the non-annotated slice and the annotated slice and a radius of the lesion.

12. The non-transitory computer readable storage medium of claim 11, wherein the distance transformation value is normalized to a range of 0 and 1, with 0 representing an edge of the lesion, and 1 representing a center of the lesion.

13. A computer system, comprising:
one or more processors; and
a memory comprising instructions for training of a convolutional neural network (CNN) in multiple stages, the instructions, when executed by the one or more processors, causing the one or more processors to:
pre-train via contrastive learning, an encoder of the CNN using an unlabeled 3D image dataset, the unlabeled 3D image dataset containing a plurality of 3D medical images, each of which includes an annotated slice and multiple non-annotated 2D slices above and below the annotated slice, the annotated 2D slice including an annotation that delineates a boundary of a lesion, wherein the unlabeled 3D image dataset comprises a plurality of slices of a same lesion, and the plurality of slices of the same lesion comprises a slice with an annotation that delineates a boundary of the lesion and remaining slices without an annotation, and wherein pre-training via contrastive learning further comprises:
masking an area of the lesion on the annotated slice based on the delineated boundary of the lesion; and
augmenting masked slices by masking a remaining slice based on distances between points on the remaining slice of the lesion and a center point of the lesion on the annotated slice; and
fine-tune the pre-trained encoder using an annotated 2D image dataset, the annotated 2D image dataset containing a plurality of 2D slices of lesions, each of which includes an annotation that delineates a boundary of a corresponding lesion.

14. The computer system of claim 13, wherein the one or more processors are further caused to:
augment positive pairs of 2D images based on a similarity between a first slice and a second slice of a same lesion.

15. The computer system of claim 14, wherein augmenting the positive pairs comprises:
determining a similarity between the first slice and the second slice;
determining whether the similarity is greater than a predetermined threshold; and
responsive to determining that the similarity is greater than the predetermined threshold, determining that the first slice and the second slice are a positive pair.

16. The computer system of claim 13, wherein masking a remaining slice comprises:
identifying the center point and a radius of the lesion on the annotated slice;
determining a distance transformation value between a point on the remaining slice and the center point of the lesion on the annotated slice;
determining whether the distance transformation value is greater than a predetermined threshold; and
responsive to determining that the distance transformation value is greater than the predetermined threshold, masking the point on the remaining slice.

17. The computer system of claim 16, wherein the predetermined threshold is determined based in part on a distance between the non-annotated slice and the annotated slice and a radius of the lesion.

* * * * *

UNITED STATES PATENT AND TRADEMARK OFFICE
CERTIFICATE OF CORRECTION

| | | |
|---|---|---|
| PATENT NO. | : 12,175,679 B2 | Page 1 of 1 |
| APPLICATION NO. | : 18/522131 | |
| DATED | : December 24, 2024 | |
| INVENTOR(S) | : Liu et al. | |

It is certified that error appears in the above-identified patent and that said Letters Patent is hereby corrected as shown below:

In the Claims

In Column 21, in Claim 10, Line 17, delete "claim 8," and insert -- claim 7, --, therefor.

Signed and Sealed this
Sixth Day of May, 2025

Coke Morgan Stewart
*Acting Director of the United States Patent and Trademark Office*